United States Patent
Zhao et al.

(10) Patent No.: US 8,415,505 B2
(45) Date of Patent: Apr. 9, 2013

(54) 2-METHYLENE-5-SUBSTITUTED-METHYLENECYCLOPENTANONE DERIVATIVES AND USE THEREOF

(75) Inventors: Linxiang Zhao, Shenyang (CN); Jingli Wang, Shenyang (CN); Zhenjun Bian, Shenyang (CN); Rui Wang, Shenyang (CN); Dan Liu, Shenyang (CN); Yongkui Jing, Shenyang (CN)

(73) Assignee: Shenyang Pharmaceutical University, Shenyang (CN)

( * ) Notice: Subject to any disclaimer, the term of this patent is extended or adjusted under 35 U.S.C. 154(b) by 0 days.

(21) Appl. No.: 12/867,223

(22) PCT Filed: Feb. 10, 2009

(86) PCT No.: PCT/CN2009/000146
§ 371 (c)(1),
(2), (4) Date: Nov. 22, 2010

(87) PCT Pub. No.: WO2009/100656
PCT Pub. Date: Aug. 20, 2009

(65) Prior Publication Data
US 2011/0060054 A1 Mar. 10, 2011

(30) Foreign Application Priority Data

Feb. 14, 2008 (CN) .......................... 2008 1 0010386

(51) Int. Cl.
C07C 49/00 (2006.01)
C07C 317/24 (2006.01)
A61K 31/122 (2006.01)

(52) U.S. Cl. ........................... 568/330; 568/31; 514/684

(58) Field of Classification Search .................... 568/31, 568/330; 514/684
See application file for complete search history.

(56) References Cited

FOREIGN PATENT DOCUMENTS

| CN | 1058258 C | 11/2000 |
| CN | 1634868 A | 7/2005 |
| EP | 0 332 178 A1 | 9/1989 |

OTHER PUBLICATIONS

Kang, Y. et al., "Synthesis of 2-(4-Methoxybenzylidene)-5-Substituted Aminomethyl Cyclopentanone and Their Antiinflammatory activity," Chinese Journal of Medicinal Chemistry, vol. 6, No. 4, pp. 250 & 252, Dec. 22, 2006 (English abstract on p. 253).

Primary Examiner — Sikarl Witherspoon
(74) Attorney, Agent, or Firm — Seed IP Law Group PLLC

(57) ABSTRACT

The invention relates to 2-methylene-5-substituted-methylenecyclopentanone derivatives of formula I, and the use thereof. The derivatives of formula I as active components are useful for preparing a medicine for the treatment and/or prevention of cancer diseases such as breast cancer, lung cancer, colon cancer, rectal cancer, stomach cancer, prostate cancer, bladder cancer, uterus cancer, pancreatic cancer and ovary cancer. The active compounds of the invention may be used as an anticancer drug alone or used in combination with one or more other antitumor drugs. A combined therapy can be carried out by administrating each therapeutic component concurrently, subsequently or separately.

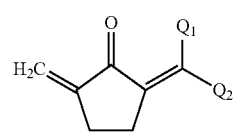

I

18 Claims, No Drawings

2-METHYLENE-5-SUBSTITUTED-METHYLENECYCLOPENTANONE DERIVATIVES AND USE THEREOF

FIELD OF THE INVENTION

The present invention belongs to the field of medicinal technique. The invention relates to 2-methylene-5-substituted-methylenecyclopentanone derivatives and use thereof. In particular, the invention relates to 2-methylene-5-substituted-methylenecyclopentanone derivatives and their uses as anticancer agents.

BACKGROUND OF THE INVENTION

Cancer, also known as malignant tumor, is a common disease that seriously threatens human health. At present, the mortality rate of cancer is still rising, but there still lacks of effective drugs treating common solid tumors.

Cells acquire the ability of unlimited proliferation due to the activation of the oncogenes, which is the main reason for carcinogenesis. It has been proved that the inhibition of the cell apoptosis pathways, which are under strict genetic and biochemical regulations, is another important reason for carcinogenesis. Through membrane blebbing, the apoptotic cells formed apoptotic bodies that are coated by cell membrane, and those apoptotic bodies are quickly cleared by phagocytes. As a result, inducing apoptosis in tumor cells can have anticancer effects without strong immune response, therefore inducing apoptosis in tumor cells has become more important in cancer treatment. In recent years, with the development of research on the mechanism of cell apoptosis, depletion of reduced glutathione (GSH) has been found in the process of inducing apoptosis of tumor cells. The level of GSH is closely related to cell apoptosis, and synthetic inhibitors and GSH conjugant have anticancer function via inducing apoptosis of tumor cells. The latest study has shown that the level of GSH in cells determines the effect of the apoptosis of human M14 melanoma cells induced by c-myc oncogene, further proving GSH plays an important role in the process of cell apoptosis.

Intracellular GSH level is relevant to cell proliferation rate. Growth rate limited tumor cells have a significantly increased demand for GSH, and the GSH levels are elevated in various human cancer tissues such as pancreas, lung, ovary, larynx, breast and liver cancer tissues compared with normal tissues in these regions. For example, the total GSH content is (17.5±2.3) nmol/mg protein in pancreatic tumor tissue, while the content is (8.8±1.4) nmol/mg in normal pancreatic tissue, P<0.004; The GSH content in liver tumor tissue is twice more than that in normal tissue, wherein the total GSH content in former is (41.9±7.2) nmol/mg protein and that in latter is (22.4±3.5) nmol, P<0.02. Although the level of GSH in tumor tissues is significantly higher than that in normal tissues, it can only meet the needs of tumor growth and proliferation. On the other hand, the level of GSH in normal cells is much higher than that needed by normal metabolism. As such, tumor cells have a much higher sensitivity to GSH depletion than normal cells. It has been reported that in 18 human neuroblastoma cell lines, when intracellular GSH levels are decreased by 90%, then these cells are subjected to apoptosis, while the function of normal cells under the same conditions is almost not affected. Therefore, it is possible to selectively induce apoptosis in tumor cells through GSH depletion.

With the advance of study on molecular biological mechanism of apoptosis, inducing apoptosis in tumor cells provides a new idea and a new pathway for tumor chemical therapy. Many apoptosis inducing agents of tumor cells are related with GSH depletion. It is also believed that intracellular GSH depletion is the common mechanism of inducing tumor cell apoptosis by various factors. Compared with the GSH level in normal cells, tumor cells contain a higher level of GSH and have a bigger demand for GSH. Therefore, theoretically, synthetic inhibitors and conjugant of GSH can selectively induce apoptosis in tumor cells when used alone, and they can reverse the multi-drug resistance of tumor cells when used in combination with other anticancer drugs, thus increase the sensitivity of tumor cells to chemotherapeutic drugs, and bring new prospect to improve the ability of the selectivity and targeting of cancer chemotherapy.

SUMMARY OF THE INVENTION

It is an objective of the present invention to provide 2-methylene-5-substituted-methylenecyclopentanones and derivatives thereof. The other objective of the invention is to provide the use of 2-methylene-5-substituted-methylenecyclopentanones and derivatives thereof for the preparation of medicaments for the treatment and/or prevention of tumors.

The invention provides the derivatives as defined by the following formula I,

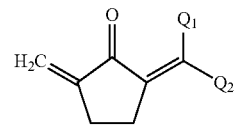

I wherein $Q_1$ is hydrogen, $Q_2$ is a straight or branched C1-C10 alkyl, C3-C7 cycloalkyl, or 5 to 10 membered heterocyclic group; wherein the heterocyclic group may contain 1 to 4 heteroatom selected from nitrogen, oxygen and sulfur, and optionally contains 1 or 2 carbon-carbon double bond or triple bond; wherein the heterocyclic group may be optionally substituted with 1 to 5 same or different $R_1$, wherein $R_1$ is independently selected from hydroxyl, halogen, nitro, cyano, carbonyl, trifluoromethyl, trifluoromethoxy, C1-C4 alkyl, C1-C4 alkoxylmethyl, C1-C4 alkoxyl, N,N-di-C1-C4 alkylamino or C3-C7 cycloalkyl; and wherein cycloalkyl may contain 1 or 2 carbon-carbon double bond or triple bond;

wherein $Q_1$ is hydrogen, $Q_2$ is substituted C6-C10 aryl, wherein aryl may be optionally substituted with 1 to 5 same or different $R_2$; wherein $R_2$ is independently selected from hydroxyl, halogen, carboxyl, amino, nitro, cyano, trifluoromethyl, trifluoromethoxy, C1-C4 alkyl, C3-C7 cycloalkyl, C1-C4 alkoxyl, C1-C3 alkylene dioxy, C1-C4 alkoxyl methyl, amino substituted with mono- or di-C1-C4 alkyl, C1-C4 alkylsulphonyl, or benzoyloxy substituted with $R_1$; wherein $R_1$ is defined as above;

wherein $Q_1$ is hydrogen, $Q_2$ is

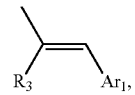

wherein $R_3$ is independently selected from hydroxyl, halogen, and C1-C4 alkyl; $Ar_1$ is C6-C10 aryl or 5 to 10 membered heteroaryl; wherein heteroaryl may contain 1 to 4 heteratoms selected from nitrogen, oxygen, or sulfur atoms; wherein aryl may be optionally substituted with 1 to 5 same or different $R_1$; wherein $R_1$ is defined as above; or $Q_1$ and $Q_2$ are the same or different substituted C6-C10 aryl, wherein aryl may be optionally substituted with 1 to 5 same or different $R_4$; $R_4$ is independently selected from halogen, nitro, cyano, haloalkyl, C1-C4 alkyl or C1-C4 alkoxyl.

The present invention also provides the following 2-methylene-5-substituted-methylenecyclopentanone derivatives having the formula I, wherein $Q_1$ is hydrogen, $Q_2$ is straight or branched C1-C10 alkyl, or C3-C7 cycloalkyl, wherein cycloalkyl may contain 1 to 2 carbon-carbon double bond or triple bond.

The present invention further provides the following 2-methylene-5-substituted-methylenecyclopentanone derivatives having the formula I, where $Q_1$ is hydrogen, $Q_2$ is phenyl, or phenyl group optionally substituted with 1 to 5 same or different $R_2$, wherein $R_2$ is independently selected from hydroxyl, halogen, carboxyl, amino, nitro, cyano, trifluoromethyl, trifluoromethoxy, C1-C4 alkyl, C3-C7 cycloalkyl, C1-C4 alkoxyl, C1-C3 alkylidene dioxyl, C1-C4 alkoxyl methyl, amino substituted with mono- or di-C1-C4 alkyl, C1-C4 alkylsulphonyl, and benzoyloxy substituted with $R_1$, wherein $R_1$ is defined as above.

The present invention further provides the following 2-methylene-5-substituted-methylenecyclopentanone derivatives having the formula of I, where $Q_1$ is hydrogen, $Q_2$ is

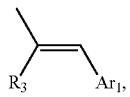

wherein $R_3$ independently selected from hydrogen, and C1-C4 alkyl; $Ar_1$ is phenyl, or phenyl group optionally substituted with 1 to 5 same or different $R_2$, $R_2$ is independently selected from hydroxyl, halogen, carboxyl, amino, nitro, cyano, trifluoromethyl, trifluoromethoxy, C1-C4 alkyl, C3-C7 cycloalkyl, C1-C4 alkoxyl, C1-C3 alkylene dioxy, C1-C4 alkoxyl methyl, amino substituted with mono- or di-C1-C4 alkyl, C1-C4 alkylsulphonyl, benzoyloxy substituted with $R_1$, wherein $R_1$ is as defined above.

The present invention also preferably provides the following 2-methylene-5-substituted-methylenecyclopentanone derivatives having the formula of I, wherein $Q_1$ and $Q_2$ are phenyl, or phenyl group optionally substituted with 1 to 5 same or different $R_4$, wherein $R_4$ is independently selected from halogen, C1-C4 alkyl, and C1-C4 alkoxyl.

Unless otherwise indicated, as used herein, the term "halogenated" means fluorine substituted, chlorine substituted, bromine substituted or iodide substituted; "alkyl" means straight or branched alkyl; "alkylene" means straight or branched alkylene; "cycloalkyl" means substituted or unsubstituted cycloalkyl; heteroaryl contains one or more heteroatoms selected from nitrogen, oxygen, or sulfur atoms, wherein each of heteroaryl ring can contain one ring or several rings, and the ring system may be aromatic, wherein heteroaryl ring can be exemplified by imidazolyl, pyridyl, pyrimidinyl, pyrazolyl, (1,2,3)- and (1,2,4)-triazolyl, pyrazinyl, tetrazolyl, furyl, thienyl, isoxazolyl, oxazolyl, pyrazolyl, pyrrolyl, thiazolyl, benzothiophenyl, benzofuryl, benzimidazolyl, benzothiazolyl, indyl, quinolyl, etc.

The derivatives of the invention as active components are useful for preparing a medicine for treatment and/or prevention of cancer diseases. The present invention also provides a method for treating or preventing above-mentioned diseases, including therapeutically effective administration dose of derivatives of present invention to patients who suffer from or are susceptible to the diseases. The clinic dosage of the 2-methylene-5-substituted-methylenecyclopentanone and derivatives thereof of above formula I depends on various factors such as the treated host, the particular administration route, and the severity of the disease, and the optimal dosage can be determined by physician who is responsible for the particular patients.

The active compound of the invention may be used alone as an anticancer drug, or used in combination with one or more other antitumor drugs. Combined therapy is carried out by administrating each therapeutic component concurrently, subsequently or separately.

Therefore, the present invention also relates to a pharmaceutical composition that contains 2-methylene-5-substituted-methylenecyclopentanone and derivatives thereof as defined above and a pharmaceutically acceptable carrier and/or adjuvant.

The following Experimental Examples and Preparative Examples further illustrate and exemplify the compounds of the invention and their preparation method. It should be understood that the following Examples are given for the purposes of illustrating this invention and are not intended as limitations thereof.

The following synthetic routes describe methods of preparing derivatives having the formula I of the invention. All raw materials can be prepared through the methods in the diagrams or prepared by common techniques which are known to ordinary technologists in organic chemistry, or can be commercially purchased. All final derivatives of the invention are prepared by the following methods or similar ones.

Route 1

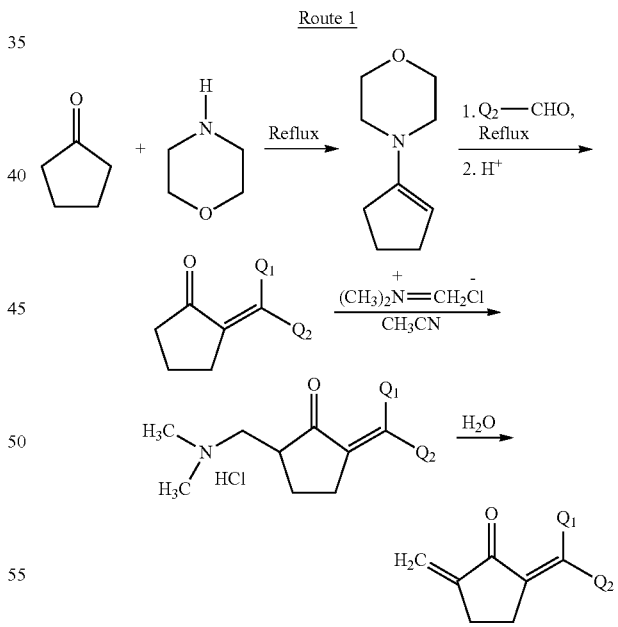

According to the derivatives of formula I of the invention, in Route 1, wherein $Q_1$ is hydrogen, $Q_2$ is phenyl, or phenyl group optionally substituted with one to five same or different $R_2$, and other substituents are as defined in the Summary of the Invention.

When $Q_1$ and $Q_2$ are phenyl, or phenyl group optionally substituted with 1 to 5 same or different $R_4$, the method of Route 2 are applied, other substituents are as defined in the Summary of the Invention.

Route 2

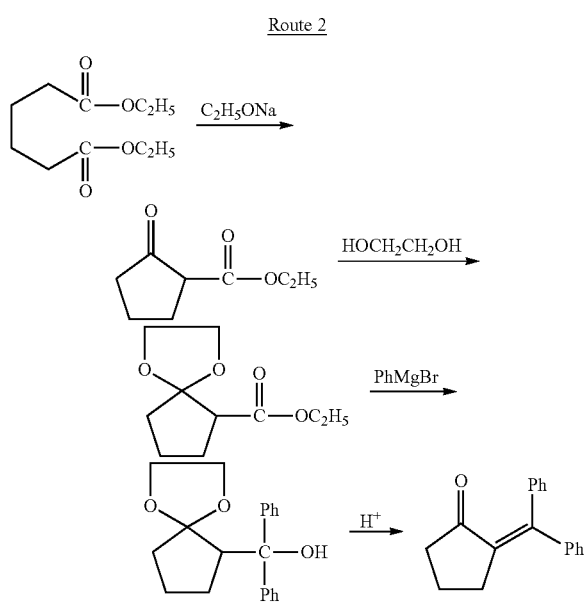

Through antitumor tests in vitro, it is found that the compounds of the invention have anticancer activities. Thus, the derivatives of formula I as active components can be useful for preparing a medicine for treatment and/or prevention for cancer diseases, such as breast cancer, lung cancer, colon cancer, rectal cancer, stomach cancer, prostate cancer, bladder career, uterus cancer, pancreatic cancer and ovary cancer.

EMBODIMENTS FOR CARRYING OUT THE INVENTION

The following Examples are given for the purpose of illustrating this invention and are not intended as limitations thereof. Proton magnetic resonance spectroscopy of derivatives were determined with the Bruker ARX-300, and their mass spectrometry were determined with Agilent 1100 LC/MSD; the reagents used were analytical grade or chemically pure.

Example 1

Preparation of 2-methylene-5-(4-chlorobenzylidene)cyclopentanone

Step A: Preparation of 2-(4-chlorobenzylidene)cyclopentanone

With reflux device installed, 36.8 g (0.24 mol) of N-cyclopentenyl morpholine, 28.1 g (0.20 mol) of p-chlorobenzaldehyde and 200 mL of benzene were added to a round bottom flask and heated under reflux for 20 h. The resulting solution was cooled to 30° C., and slowly stirred while 62 mL of hydrochloric acid (6 mol/L) was added. After stirring for 2 h at room temperature, the benzene layer was separated and washed with water to neutral, and dried over anhydrous sodium sulfate overnight. Then the mixture was filtered to remove anhydrous sodium sulfate, and benzene was recovered by evaporation under reduced pressure. The residue was cooled and solidified, then recrystallized in 95% ethanol to yield 32.9 g of light yellow flaky crystal product with a yield of 66.3%.

Step B: Preparation of 2-(4-chlorobenzylidene)-5-dimethylaminomethyl cyclopentanone hydrochloride 6.2 g (0.03 mol) of 2-(4-chlorobenzylidene)cyclopeantanone was dissolved in 30 mL anhydrous acetonitrile and treated with 8.4 g (0.09 mol) of N,N-dimethyl-methylene ammonium chloride under refluxing, refluxed for 12 h to solidify, then suction filtered, dried and recrystallized in acetonitrile/chloroform to yield 8.1 g of the white solid with a yield of 90%.

Step C: Preparation of 2-methylene-5-(4-chlorobenzylidene)cyclopentanone 3 g (0.01 mmol) of 2-(4-chlorobenzylidene)-5-dimethylaminomethyl cyclopentanone hydrochloride was dissolved in 50 mL distilled water, stirred for 72 h at room temperature, and then suction filtered and vacuum dried to yield a solid product, which was recrystallized in petroleum ether to yield 1.5 g light yellow flaky crystal with a yield of 68%.
MS: $M^+$ 218.
$^1$H-NMR (CDCl$_3$, δ ppm): 2.82 (m, 2H), 2.97 (m, 2H), 5.49 (s, 1H), 6.19 (s, 1H), 7.40 (d, 2H, J=8.4 Hz), 7.51 (m, 3H).

Example 2

Preparation of 2-methylene-5-(4-methoxybenzylidene)-cyclopentanone

Step A: Preparation of 2-(4-methoxybenzylidene)cyclopentanone

With reflux device installed, 36.8 g (0.24 mol) of N-cyclopentenyl morpholine, 27.2 g (0.20 mol) of 4-methoxybenzaldehyde and 200 mL of benzene were added to a round bottom flask and heated under reflux for 20 h. The resulting solution was cooled to 30° C., and slowly stirred while 62 mL of hydrochloric acid (6 mol/L) was added. After stirring for 2 h at room temperature, the benzene layer was separated and washed with water to neutral, and dried over anhydrous sodium sulfate overnight. Then the mixture was filtered and benzene was recovered by evaporation under reduced pressure. The residue was cooled and solidified, then recrystallized in cyclohexane/ethanol to yield light yellow flaky crystal product with a yield of 76.3%.

Step B: Preparation of 2-(4-methoxybenzylidene)-5-dimethylaminomethyl cyclopentanone hydrochloride 6.1 g (0.03 mol) of 2-(4-methoxybenzylidene)cyclopeantanone was dissolved in 30 mL anhydrous acetonitrile and treated with 8.4 g (0.09 mol) of N,N-dimethyl-methylene ammonium chloride under refluxing, refluxed for 12 h to yield a solid product, then suction filtered and dried, and recrystallized in acetonitrile/chloroform to give 2-(4-methoxybenzylidene)-5-dimethylaminomethyl cyclopentanone hydrochloride with a yield of 86.2%.

Step C: Preparation of 2-methylene-5-(4-methoxybenzylidene)cyclopentanone 3 g (0.01 mol) of 2-(4-methoxybenzylidene)-5-dimethylaminomethyl cyclopentanone hydrochloride was dissolved in 50 mL, distilled water, stirred for 72 h at room temperature and suction filtered to yield a solid product which was vacuum dried and recrystallized in petroleum ether to yield light yellow powder crystal with a yield of 70.0%.

MS: M+ 214.

1H-NMR (CDCl3, δ ppm): 2.82 (m, 2H), 3.00 (m, 2H), 3.84 (s, 3H, —OCH3), 5.45 (s, 1H), 6.17 (s, 1H), 6.96 (d, 2H, J=8.7 Hz), 7.54 (m, 3H).

Example 3

Preparation of
2-methylene-5-benzylidene-cyclopentanone

Step A: Preparation of
2-benzylidene-cyclopentanone

With reflux device installed, 36.8 g (0.24 mol) of N-cyclopentenyl morpholine, 27.2 g (0.20 mol) of benzaldehyde and 200 mL of benzene were added to a round bottom flask and heated under reflux for 20 h. The resulting solution was cooled to 30° C., and slowing stirring while 62 mL of hydrochloric acid (6 mol/L) was added to the solution. After stirring for 2 h at room temperature, the benzene layer was separated and washed with water to neutral, and dried over anhydrous sodium sulfate overnight. Then the mixture was filtered and benzene was recovered by evaporation under reduced pressure. The residue was cooled and solidified, then recrystallized in cyclohexane/ethanol to yield 2-benzylidene-cyclopentanone with a yield of 84.6%.

Step B: Preparation of
2-benzylidene-5-dimethylaminomethyl
cyclopentanone hydrochloride 5.2 g (0.03 mol) of 2-benzylidene-cyclopentanone was dissolved in 30 mL anhydrous acetonitrile, treated with 8.4 g (0.09 mol) of N,N-dimethyl-methylene ammonium chloride under refluxing, refluxed for 12 h to yield a solid product, then suction filtered and dried, and recrystallized in acetonitrile/chloroform to give 2-benzylidene-5-dimethylaminomethyl cyclopentanone hydrochloride with a yield of 76.2%.

Step C: Preparation of
2-methylene-5-benzylidenecyclopentanone 2.7 g (0.01 mol) of 2-benzylidene-5-dimethylaminomethyl cyclopentanone hydrochloride was dissolved in 50 mL distilled water, stirred for 72 h at room temperature, and then suction filtered to yield a solid product which was vacuum dried and recrystallized in petroleum ether to yield light yellow powder crystal with a yield of 62.0%.

MS: M+ 184.

1H-NMR (CDCl3, δ ppm): 2.82 (m, 2H), 3.02 (m, 2H), 5.48 (s, 1H), 6.19 (s, 1H), 7.43 (m, 3H), 7.56 (m, 3H).

Example 4

Preparation of
2-methylene-5-(4-methylbenzylidene)cyclopentanone

Step A: Preparation of
2-(4-methylbenzylidene)cyclopentanone

With reflux device installed, 36.8 g (0.24 mol) of N-cyclopentenyl morpholine, 24.0 g (0.20 mol) of 4-methylbenzaldehyde and 200 mL of benzene were added to a round bottom flask and heated under reflux for 20 h. The resulting solution was cooled to 30° C., and slowly stirred while 62 mL of hydrochloric acid (6 mol/L) was added. After stirring for 2 h at room temperature, the benzene layer was separated and washed with water to neutral, and dried over anhydrous sodium sulfate overnight. Then the mixture was filtered and benzene was recovered by evaporation under reduced pressure. The residue was cooled and solidified, then recrystallized in cyclohexane/ethanol to yield light yellow flaky crystal product with a yield of 94.5%.

Step B: Preparation of
2-(4-methylbenzylidene)-5-dimethylaminomethyl
cyclopentanone hydrochloride 5.6 g (0.03 mol) of 2-(4-methylbenzylidene)cyclopentanone was dissolved in 30 mL anhydrous acetonitrile, treated with 8.4 g (0.09 mol) of N,N-dimethyl-methylene ammonium chloride under refluxing, refluxed for 12 h to yield a solid product, then suction filtered and dried, and recrystallized in acetonitrile/chloroform to yield 2-(4-methylbenzylidene)-5-dimethylaminomethyl-cyclopentanone hydrochloride with a yield of 75.2%.

Step C: Preparation of
2-methylene-5-(4-methylbenzylidene)cyclopentanone 2.8 g (0.01 mol) of 2-(4-methoxybenzylidene)-5-dimethylaminomethyl cyclopentanone hydrochloride was dissolved in 50 mL distilled water, stirred for 72 h at room temperature, then suction filtered to yield a solid product which was vacuum dried and recrystallized in petroleum ether to yield as light yellow powder crystal with a yield of 61.6%.

MS: M+ 198.

1H-NMR (CDCl3, δ ppm): 2.35 (s, 3H, —CH3), 2.77 (m, 2H), 2.95 (m, 2H), 5.52 (s, 1H), 5.98 (s, 1H), 7.30 (d, 2H, J=7.8 Hz), 7.37 (m, 1H), 7.56 (d, 2H, J=7.8 Hz).

Example 5

Preparation of
2-methylene-5-(3-methoxybenzylidene)cyclopentanone

Step A: Preparation of
2-(3-methoxybenzylidene)cyclopentanone

With reflux device installed, 36.8 g (0.24 mol) of N-cyclopentenyl morpholine, 27.2 g (0.20 mol) of 3-methoxybenzaldehyde and 200 mL of benzene were added to a round bottom flask and heated under refluxing for 20 h. The resulting solution was cooled to 30° C., and slowly stirred while 62 mL of hydrochloric acid (6 mol/L) was added. After stirring for 2 h at room temperature, the benzene layer was separated and washed with water to neutral, and dried over anhydrous sodium sulfate overnight. Then the mixture was filtered to remove anhydrous sodium sulfate and benzene was recovered by evaporation under reduced pressure. The residue was cooled and solidified, then recrystallized in cyclohexane/ethanol to yield a light yellow flaky crystal product with a yield of 66.0%.

Step B: Preparation of
2-(3-methoxybenzylidene)-5-dimethylaminomethyl
cyclopentanone hydrochloride 6.1 g (0.03 mol) of 2-(3-methoxybenzylidene)cyclopentanone was dissolved in 30 mL anhydrous acetonitrile, treated with 8.4 g (0.09 mol) of N,N-dimethyl-methylene ammonium chloride under refluxing, refluxed for 12 h to yield a solid product, which was filtered, dried and recrystallized in acetonitrile/chloroform to yield 2-(4-methoxybenzylidene)-5-dimethylaminomethyl cyclopentanone hydrochloride with a yield of 76.8%.

Step C: Preparation of 2-methylene-5-(3-methoxybenzylidene)cyclopentanone 3 g (0.01 mol) of 2-(3-methoxybenzylidene)-5-dimethylaminomethyl cyclopentanone hydrochloride was dissolved in 50 mL distilled water, stirred for 72 h at room temperature, then suction filtered to yield a solid product which was vacuum dried and recrystallized in petroleum ether to yield light yellow powder crystal with a yield of 70.0%.

MS: M$^+$ 214.

$^1$H-NMR (CDCl$_3$, δ ppm): 2.77 (m, 2H), 2.97 (m, 2H), 3.79 (s, 3H, —OCH$_3$), 5.52 (s, 1H), 5.99 (s, 1H), 7.00 (d, 1H, J=7.8 Hz), 7.22 (m, 2H), 7.40 (m, 2H).

Example 6

Preparation of 2-methylene-5-(4-bromobenzylidene)cyclopentanone

Step A: Preparation of 2-(4-bromobenzylidene)cyclopentanone

With reflux device installed, 36.8 g (0.24 mol) of N-cyclopentenyl morpholine, 0.20 mol of 4-bromobenzaldehyde and 200 mL of benzene were added to a round bottom flask and heated under reflux for 20 h. The resulting solution was cooled to 30° C., and slowly stirred while 62 mL of hydrochloric acid (6 mol/L) was added. After stirring for 2 h at room temperature, the benzene layer was separated and washed with water to neutral, and dried over anhydrous sodium sulfate overnight. Then the mixture was filtered and benzene was recovered by evaporation under reduced pressure. The residue was cooled and solidified, then recrystallized in cyclohexane/ethanol to yield a light yellow flaky crystal product with a recovery of 71.2%.

Step B: Preparation of 2-(4-bromobenzylidene)-5-dimethylaminomethyl cyclopentanone hydrochloride 0.03 mol of 2-(4-bromobenzylidene)cyclopeantanone was dissolved in 30 mL anhydrous acetonitrile, treated with 8.4 g (0.09 mol) of N,N-dimethyl-methylene ammonium chloride under refluxing, refluxed for 12 h to yield a solid product, then suction filtered, dried and recrystallized in acetonitrile/chloroform to yield 2-(4-bromobenzylidene)-5-dimethylaminomethyl cyclopentanone hydrochloride with a yield of 85.0%.

Step C: Preparation of 2-methylene-5-(4-bromobenzylidene)cyclopentanone 0.01 mol of 2-(4-bromobenzylidene)-5-dimethylaminomethyl cyclopentanone hydrochloride was dissolved in 50 mL distilled water, stirred for 72 h at room temperature, and filtered to yield a solid product which was vacuum dried and recrystallized in petroleum ether to yield light yellow powder crystal with a yield of 72.1%.

MS: M$^+$ 265.

$^1$H-NMR (CDCl$_3$, δ ppm): 2.79 (m, 2H), 2.94 (m, 2H), 5.55 (s, 1H), 6.01 (s, 1H), 7.37 (t, 1H, J=2.7 Hz), 7.67 (m, 4H).

Example 7

Preparation of 2-methylene-5-(2-methoxybenzylidene)cyclopentanone

Step A: Preparation of 2-(2-methoxybenzylidene)cyclopentanone

With reflux device installed, 36.8 g (0.24 mol) of N-cyclopentenyl morpholine, 27.2 g (0.20 mol) of 2-methoxyzaldehyde and 200 mL of benzene were added to a round bottom flask and heated under reflux for 20 h. The resulting solution was cooled to 30° C., and slowly stirred while 62 mL of hydrochloric acid (6 mol/L) was added. After stirring for 2 h at room temperature, the benzene layer was separated and washed with water to neutral, and dried over anhydrous sodium sulfate overnight. Then the mixture was filtered and benzene was recovered by evaporation under reduced pressure. The residue was cooled and solidified, then recrystallized in cyclohexane/ethanol to yield a light yellow flaky crystal product with a yield of 80.0%.

Step B: Preparation of 2-(2-methoxybenzylidene)-5-dimethylaminomethyl cyclopentanone hydrochloride 6.1 g (0.03 mol) of 2-(2-methoxybenzylidene)cyclopeantanone was dissolved in 30 mL anhydrous acetonitrile, treated with 8.4 g (0.09 mol) of N,N-dimethyl-methylene ammonium chloride under refluxing, refluxed for 12 h to yield a solid product which was suction filtered, dried and recrystallized in acetonitrile/chloroform to yield 2-(2-methoxybenzylidene)-5-dimethylaminomethyl cyclopentanone hydrochloride with a yield of 75.3%.

Step C: Preparation of 2-methylene-5-(2-methoxybenzylidene)cyclopentanone 3 g (0.01 mol) of 2-(2-methoxybenzylidene)-5-dimethylaminomethylcyclopentanone hydrochloride was dissolved in 50 mL distilled water, stirred for 72 h at room temperature, suction filtered to yield a solid product which was vacuum dried and recrystallized in petroleum ether to yield a light yellow powder crystal with a yield of 81.2%.

MS: M$^+$ 214.

$^1$H-NMR (CDCl$_3$, δ ppm): 2.77 (t, 2H), 2.94 (t, 2H), 3.88 (s, 3H), 5.44 (s, 1H), 6.17 (s, 1H), 6.93 (d, 1H, J=8 Hz), 6.98 (t, 1H), 7.34 (t, 1H), 7.50 (d, 1H, J=8 Hz), 7.95 (s, 1H).

Example 8

Preparation of 2-methylene-5-(4-ethoxybenzylidene)cyclopentanone

Step A: Preparation of 2-(4-ethoxybenzylidene)cyclopentanone

With reflux device installed, 36.8 g (0.24 mol) of N-cyclopentenyl morpholine, 0.20 mol of 4-ethoxybenzaldehyde and 200 mL of benzene were added to a round bottom flask and heated under reflux for 20 h. The resulting solution was cooled to 30° C., and slowly stirred while 62 mL of hydrochloric acid (6 mol/L) was added. After stirring for 2 h at room temperature, the benzene layer was separated and washed with water to neutral, and dried over anhydrous sodium sulfate overnight. Then the mixture was filtered to remove anhydrous sodium sulfate and benzene was recovered by evaporation under reduced pressure. The residue was cooled and solidified, then recrystallized in cyclohexane/ethanol to yield a light yellow flaky crystal product with a yield of 62.4%.

Step B: Preparation of 2-(4-ethoxybenzylidene)-5-dimethylaminomethyl cyclopentanone hydrochloride 0.03 mol of 2-(4-ethoxybenzylidene)cyclopeantanone was dissolved in 30 mL anhydrous acetonitrile, treated with 8.4 g (0.09 mol) of N,N-dimethyl-methylene ammonium chloride under refluxing, refluxed for 12 h to yield a solid product which was suction filtered, dried and recrystallized in acetonitrile/chloroform to yield 2-(4-ethoxybenzylidene)-5-dimethylaminomethyl cyclopentanone hydrochloride with a yield of 90.0%.

Step C: Preparation of 2-methylene-5-(4-ethoxybenzylidene)cyclopentanone 0.01 mol of 2-(4-ethoxybenzylidene)-5-dimethylaminomethyl cyclopentanone hydrochloride was dissolved in 50 mL distilled water, stirred for 72 h at room temperature, suction filtered to yield a solid product which was vacuum dried and recrystallized in petroleum ether to yield a light yellow powder crystal with a yield of 83.3%.

MS: M+ 244.

$^1$H-NMR (CDCl$_3$, δ ppm): 1.45 (t, 3H), 2.80 (t, 2H), 2.98 (t, 2H), 4.08 (m, 2H), 5.44 (s, 1H), 6.16 (s, 1H), 6.94 (d, 2H), 7.52 (t, 3H).

Example 9

Preparation of 2-methylene-5-(4-propoxybenzylidene)cyclopentanone

Step A: Preparation of 2-(4-propoxybenzylidene)cyclopentanone

With reflux device installed, 36.8 g (0.24 mol) of N-cyclopentenyl morpholine, 0.20 mol of 4-propoxybenzaldehyde and 200 mL of benzene were added to a round bottom flask and heated under reflux for 20 h. The resulting solution was cooled to 30° C., and slowly stirred while 62 mL of hydrochloric acid (6 mol/L) was added. After stirring for 2 h at room temperature, the benzene layer was separated and washed with water to neutral, and dried over anhydrous sodium sulfate overnight. Then the mixture was filtered to remove anhydrous sodium sulfate and benzene was recovered by evaporation under reduced pressure. The residue was cooled and solidified, then recrystallized in cyclohexane/ethanol to yield a light yellow flaky crystal product with a yield of 71.9%.

Step B: Preparation of 2-(4-propoxybenzylidene)-5-dimethylaminomethyl cyclopentanone hydrochloride 0.03 mol of 2-(4-propoxybenzylidene)cyclopeantanone was dissovled in 30 mL anhydrous acetonitrile, treated with 8.4 g (0.09 mol) of N,N-dimethyl-methylene ammonium chloride under refluxing, refluxed for 12 h to yield a solid product which was suction filtered, dried and recrystallized in acetonitrile/chloroform to yield 2-(4-propoxybenzylidene)-5-dimethylaminomethyl cyclopentanone hydrochloride with a yield of 88.7%.

Step C: Preparation of 2-methylene-5-(4-propoxybenzylidene)cyclopentanone 0.01 mol of 2-(4-propoxybenzylidene)-5-dimethylaminomethyl cyclopentanone hydrochloride was dissolved in 50 mL distilled water, stirred for 72 h at room temperature and suction filtered to yield a solid product which was vacuum dried and recrystallized in petroleum ether to yield light yellow powder crystal with a yield of 59.8%.

MS: M+ 242.

$^1$H-NMR (CDCl$_3$, δ ppm): 1.04 (t, 3H, J=8 Hz), 1.82 (m, 2H, J=8 Hz), 2.81 (m, 2H), 2.98 (m, 2H), 3.97 (t, 2H, J=8 Hz), 5.44 (s, 1H), 6.16 (s, 1H), 6.94 (d, 2H, J=8.5 Hz), 7.53 (d, 3H, J=8.5 Hz).

Example 10

Preparation of 2-methylene-5-(4-methanesulfonyl-benzylidene)cyclopentanone

Step A: Preparation of 2-(4-methanesulfonylbenzylidene)cyclopentanone

With reflux device installed, 36.8 g (0.24 mol) of N-cyclopentenyl morpholine, 0.20 mol of 4-methanesulfonylbenzaldehyde and 200 mL of benzene were added to a round bottom flask and heated under reflux for 20 h. The resulting solution was cooled to 30° C., and slowly stirred while 62 mL of hydrochloric acid (6 mol/L) was added. After stirring for 2 h at room temperature, the benzene layer was separated and washed with water to neutral, and dried over anhydrous sodium sulfate overnight. Then the mixture was filtered to remove anhydrous sodium sulfate and benzene was recovered by evaporation under reduced pressure. The residue was cooled and solidified, then recrystallized in cyclohexane/ethanol to yield a light yellow flaky crystal product with a yield of 69.9%.

Step B: Preparation of 2-(4-methanesulfonylbenzylidene)-5-dimethylamino methyl cyclopentanone hydrochloride 0.03 mol of 2-(4-methanesulfonyl benzylidene)cyclopeantanone was dissovled in 30 mL anhydrous acetonitrile, treated with 8.4 g (0.09 mol) of N,N-dimethyl-methylene ammonium chloride under refluxing, refluxed for 12 h to yield a solid product which was suction filtered, dried and recrystallized in acetonitrile/chloroform to yield 2-(4-methanesulfonylbenzylidene)-5-dimethylaminomethylcyclopentanone hydrochloride with a yield of 76.5%.

Step C

Preparation of 2-methylene-5-(4-methanesulfonyl-benzylidene)cyclopentanone 0.01 mol of 2-(4-methanesulfonyl benzylidene)-5-dimethylamino-methyl cyclopentanone hydrochloride was dissolved in 50 mL distilled water, stirred for 72 h at room temperature, and suction filtered to yield a solid product which was vacuum dried and recrystallized in petroleum ether to yield light yellow powder crystal with a yield of 66.9%.

MS: [M+1] 263.

$^1$H-NMR (CDCl$_3$, δ ppm): 2.86 (s, 2H), 3.02 (m, 2H), 3.07 (s, 3H), 5.54 (s, 1H), 6.24 (s, 1H), 7.53 (s, 1H), 7.73 (d, 2H, J=8.5 Hz), 7.98 (d, 2H, J=8.5 Hz).

Example 11

Preparation of 2-methylene-5-(4-N,N-dimethylbenzylidene)cyclopentanone

Step A: Preparation of 2-(4-N,N-dimethylbenzylidene)cyclopentanone

With reflux device installed, 36.8 g (0.24 mol) of N-cyclopentenyl morpholine, 0.20 mol of 4-N,N-dimethylbenzaldehyde and 200 mL of benzene were added to a round bottom flask and heated under refluxing for 20 h. The resulting solution was cooled to 30° C., and slowly stirred while 62 mL of hydrochloric acid (6 mol/L) was added. After stirring for 2 h at room temperature, the benzene layer was separated and washed with water to neutral, and dried over anhydrous sodium sulfate overnight. Then the mixture was filtered to remove anhydrous sodium sulfate and benzene was recovered by evaporation under reduced pressure. The residue was cooled and solidified, then recrystallized in cyclohexane/ethanol to yield a light yellow flaky crystal product with a yield of 80.3%.

Step B: Preparation of 2-(4-N,N-dimethylbenzylidene)-5-dimethylaminomethyl cyclopentanone hydrochloride 0.03 mol of 2-(4-N,N-dimethylbenzylidene)cyclopeantanone was dissolved in 30 mL anhydrous acetonitrile, treated with 8.4 g (0.09 mol) of N,N-dimethyl-methylene ammonium chloride under refluxing, refluxed for 12 h to yield a solid product which was suction filtered, dried and recrystallized in acetonitrile/chloroform to yield 2-(4-N,N-dimethylbenzylidene)-5-dimethylaminomethyl cyclopentanone hydrochloride with a yield of 71.3%.

Step C: Preparation of 2-methylene-5-(4-N,N-dimethylbenzylidene)cyclopentanone 0.01 mol of 2-(4-N,N-dimethylbenzylidene)-5-dimethylaminomethyl cyclopentanone hydrochloride was dissolved in 50 mL distilled water, stirred for 72 h at room temperature, and suction filtered to yield a solid product which was vacuum dried and recrystallized in petroleum ether to yield light yellow powder crystal with a yield of 80.0%.
MS: M$^+$ 227.
$^1$H-NMR (CDCl$_3$, δ ppm): 2.80 (m, 2H), 2.94 (m, 2H), 3.05 (s, 6H), 5.40 (s, 1H), 6.13 (s, 1H), 6.76 (d, 2H, J=9 Hz), 7.50-7.53 (t, 3H, J=9 Hz).

Example 12

Preparation of 2-methylene-5-(2-hydroxy-4-methoxybenzylidene)cyclopentanone

Step A: Preparation of 2-(2-hydroxy-4-methoxybenzylidene)cyclopentanone

With reflux device installed, 36.8 g (0.24 mol) of N-cyclopentenyl morpholine, 0.20 mol of 2-hydroxy-4-methoxybenzaldehyde and 200 mL of benzene were added to a round bottom flask and heated under reflux for 20 h. The resulting solution was cooled to 30° C., and slowly stirred while 62 mL of hydrochloric acid (6 mol/L) was added. After stirring for 2 h at room temperature, the benzene layer was separated and washed with water to neutral, and dried over anhydrous sodium sulfate overnight. Then the mixture was filtered to remove anhydrous sodium sulfate and benzene was recovered by evaporation under reduced pressure. The residue was cooled and solidified, then recrystallized in cyclohexane/ethanol to yield a light yellow flaky crystal product with a yield of 70.6%.

Step B: Preparation of 2-(2-hydroxy-4-methoxybenzylidene)-5-dimethylaminomethyl cyclopentanone hydrochloride 0.03 mol of 2-(2-hydroxy-4-methoxybenzylidene)cyclopeantanone was dissolved in mL anhydrous acetonitrile, treated with 8.4 g (0.09 mol) of N,N-dimethyl-methylene ammonium chloride under refluxing, and refluxed for 12 h to yield a solid product which was suction filtered, dried and recrystallized in acetonitrile/chloroform to yield 2-(2-hydroxy-4-methoxybenzylidene)-5-dimethylaminomethyl cyclopentanone hydrochloride with a yield of 82.6%.

Step C

Preparation of 2-methylene-5-(2-hydroxy-4-methoxybenzylidene)cyclopentanone 0.01 mol of 2-(2-hydroxy-4-methoxybenzylidene)-5-dimethylaminomethyl cyclopentanone hydrochloride was dissolved in 50 mL distilled water, stirred for 72 h at room temperature and suction filtered to yield a solid product which was vacuum dried and recrystallized in petroleum ether to yield light yellow powder crystal with a yield of 73.5%.
MS: M$^+$ 230.
$^1$H-NMR (CDCl$_3$, δ ppm): 2.80 (t, 2H), 2.95 (t, 2H), 3.83 (s, 3H), 5.47 (s, 1H), 6.19 (s, 1H), 6.52 (s, 2H), 47.46 (d, 2H, J=10 Hz), 8.10 (s, 1H).

Example 13

Preparation of 2-methylene-5-(3-hydroxy-4-methoxybenzylidene)cyclopentanone

Step A Preparation of 2-(2-hydroxy-4-methoxybenzylidene)cyclopentanone

With reflux device installed, 36.8 g (0.24 mol) of N-cyclopentenyl morpholine, 0.20 mol of 3-hydroxy-4-methoxybenzaldehyde and 200 mL benzene were added to a round bottom flask and heated under reflux for 20 h. The resulting solution was cooled to 30° C. and slowly stirred while 62 mL of hydrochloric acid (6 mol/L) was added. After stirring for 2 h at room temperature, the benzene layer was separated and washed with water to neutral, and dried over anhydrous sodium sulfate overnight. Then the mixture was filtered to remove anhydrous sodium sulfate and benzene was recovered by evaporation under reduced pressure. The residue was cooled and solidified, then recrystallized in cyclohexane/ethanol to yield a light yellow flaky crystal product with a yield of 90.4%.

Step B Preparation of 2-(3-hydroxy-4-methoxybenzylidene)-5-dimethylaminomethyl cyclopentanone hydrochloride 0.03 mol of 2-(3-hydroxy-4-methoxybenzylidene)cyclopentanone was dissolved in mL anhydrous acetonitrile, treated with 8.4 g (0.09 mol) of N,N-dimethyl-methylene ammonium chloride under refluxing, refluxed for 12 h to yield a solid product which was suction filtered, dried and recrystallized in acetonitrile/chloroform to yield 2-(3-hydroxy-4-methoxybenzylidene)-5-dimethylaminomethyl cyclopentanone hydrochloride with a yield of 93.5%.

Step C

Preparation of 2-methylene-5-(3-hydroxy-4-methoxybenzylidene)cyclopentanone 0.01 mol 2-(3-hydroxy-4-methoxybenzylidene)-5-(dimethylaminomethyl)-cyclopentanone hydrochloride was dissolved in 50 mL distilled water, stirred for 72 h at room temperature, then suction filtered to yield a solid product which was vacuum dried and recrystallized in petroleum ether to yield light yellow powder crystal with a yield of 81.3%.

MS: $M^+$ 230.
$^1$H-NMR (CDCl$_3$, δ ppm): 2.82 (m, 2H), 2.98 (m, 2H), 3.94 (s, 3H), 5.44 (s, 1H), 5.62 (s, 1H), 6.16 (s, 1H), 6.90 (d, 1H, J=8.4 Hz), 7.11 (dd, 1H), 7.20 (d, 1H), 7.46 (t, 1H).

Example 14

Preparation of 2-methylene-5-(4-hydroxy-3-methoxybenzylidene)cyclopentanone

Step A Preparation of 2-(4-hydroxy-3-methoxybenzylidene)cyclopentanone

With reflux device installed, 36.8 g (0.24 mol) of N-cyclopentenyl morpholine, 0.20 mol of 4-hydroxy-3-methoxybenzaldehyde and 200 mL benzene were added to a round bottom flask and heated under refluxing for 20 h. The resulting solution was cooled to 30° C. and slowly stirred while 62 mL of hydrochloric acid (6 mol/L) was added. After stirring for 2 h at room temperature, the benzene layer was separated and washed with water to neutral, and dried over anhydrous sodium sulfate overnight. Then the mixture was filtered to remove anhydrous sodium sulfate and benzene was recovered by evaporation under reduced pressure. The residue was cooled and solidified, then recrystallized in cyclohexan/ethanol to yield a light yellow flaky crystal product with a yield of 92.6%

Step B Preparation of 2-(4-hydroxy-3-methoxybenzylidene)-5-dimethylamino-methyl cyclopentanone hydrochloride 0.03 mol of 2-(4-hydroxy-3-methoxybenzylidene)cyclopentanone was dissolved in mL anhydrous acetonitrile, treated with 8.4 g (0.09 mol) of N,N-dimethyl-methylene ammonium chloride under refluxing, refluxed for 12 h to yield a solid product which was suction filtered, dried and recrystallized in acetonitrile/chloroform to yield 2-(4-hydroxy-3-methoxybenzylidene)-5-dimethylaminomethyl-cyclopentanone hydrochloride with a yield of 91.1%.

Step C

Preparation of 2-methylene-5-(4-hydroxy-3-methoxybenzylidene)cyclopentanone 0.01 mol 2-(4-hydroxy-3-methoxybenzylidene)-5-(dimethylaminomethyl)cyclopentanone hydrochloride was dissolved in 50 mL distilled water, stirred for 72 h at room temperature, then suction filtered to yield a solid product which was vacuum dried and recrystallized in petroleum ether to yield light yellow powder crystal with a yield of 86.2%.

MS: $M^+$ 230.
$^1$H-NMR (CDCl$_3$, δ ppm): 2.82 (m, 2H), 2.97 (m, 2H), 3.94 (s, 3H), 5.43 (d, 1H), 5.62 (s, 1H), 6.16 (s, 1H) 6.89 (d, 1H, J=8.4 Hz), 7.09 (d, 1H), 7.18 (d, 1H), 7.46 (m, 1H).

Example 15

Preparation of 2-methylene-5-(2,3-dimethoxybenzylidene)cyclopentanone

Step A Preparation of 2-(2,3-dimethoxybenzylidene)cyclopentanone

With reflux device installed, 36.8 g (0.24 mol) of N-cyclopentenyl morpholine, 0.20 mol of 2,3-dimethoxybenzaldehyde and 200 mL benzene were added to a round bottom flask and heated under reflux for 20 h. The resulting solution was cooled to 30° C. and slowly stirred while 62 mL of hydrochloric acid (6 mol/L) was added. After stirring for 2 h at room temperature, the benzene layer was separated and washed with water to neutral, and dried over anhydrous sodium sulfate overnight. Then the mixture was filtered to remove anhydrous sodium sulfate and benzene was recovered by evaporation under reduced pressure. The residue was cooled and solidified, then recrystallized in cyclohexane/ethanol to yield a light yellow flaky crystal product with a yield of 80.3%.

Step B

Preparation of 2-(2,3-dimethoxybenzylidene)-5-(dimethylaminomethyl)-cyclopentanone hydrochloride 0.03 mol of 2-(2,3-dimethylbenzylidene)cyclopentanone was dissolved in 30 mL anhydrous acetonitrile, treated with 8.4 g (0.09 mol) of N,N-dimethyl-methylene ammonium chloride under refluxing, refluxed for 12 h to yield a solid product which was then suction filtered, dried and recrystallized in acetonitrile/chloroform to yield 2-(2,3-dimethoxybenzylidene)-5-(dimethylaminomethyl)cyclopentanone hydrochloride with a yield of 86.1%.

Step C Preparation of 2-methylene-5-(2,3-dimethoxybenzylidene)cyclopentanone 0.01 mol 2-(2,3-dimethoxybenzylidene)-5-(dimethylaminomethyl)cyclopentanone hydrochloride was dissolved in 50 mL distilled water, stirred for 72 h at room temperature, then suction filtered to yield a solid product which was vacuum dried and recrystallized in petroleum ether to yield light yellow powder crystal with a yield of 71.0%.

MS: $M^+$ 244,
$^1$H-NMR (CDCl$_3$, δ ppm): 2.78 (m, 2H), 2.92 (m, 2H), 3.85 (s, 3H), 3.89 (s, 3H), 5.47 (s, 1H), 6.18 (s, 1H), 6.97 (m, 1H), 7.12 (m, 2H), 7.87 (s, 1H).

Example 16

Preparation of 2-methylene-5-(2,4-dimethoxybenzylidene)cyclopentanone

Step A Preparation of 2-(2,4-dimethoxybenzylidene)cyclopentanone

With reflux device installed, 36.8 g (0.24 mol) of N-cyclopentenyl morpholine, 0.20 mol of 2,4-dimethoxybenzaldehyde and 200 mL benzene were added to a round bottom flask and heated under reflux for 20 h. The resulting solution was cooled to 30° C. and slowly stirred while 62 mL of hydrochloric acid (6 mol/L) was added. After stirring for 2 h at room temperature, the benzene layer was separated and washed with water to neutral, and dried over anhydrous sodium sulfate overnight. Then the mixture was filtered to remove anhydrous sodium sulfate and benzene was recovered by evaporation under reduced pressure. The residue was cooled and solidified, then recrystallized in cyclohexane/ethanol to yield a light yellow flaky crystal product with a yield of 71.2%.

Step B Preparation of 2-(2,4-dimethoxybenzylidene)-5-dimethylaminomethyl-cyclopentanone hydrochloride 0.03 mol of 2-(2,4-dimethoxybenzylidene)cyclopentanone was dissolved in 30 mL anhydrous acetonitrile, treated with 8.4 g (0.09 mol) of N,N-dimethyl-methylene ammonium chloride under refluxing, refluxed for 12 h to yield a solid product which was then suction filtered, dried and recrystallized in acetonitrile/chloroform to give 2-(2,4-dimethoxybenzylidene)-5-dimethylaminomethyl-cyclopentanone hydrochloride with a yield of 73.3%.

Step C Preparation of 2-methylene-5-(2,4-dimethoxybenzylidene)cyclopentanone 0.01 mol 2-(2,4-dimethoxybenzylidene)-5-dimethylaminomethyl-cyclopentanone hydrochloride was dissolved in 50 mL distilled water, stirred for 72 h at room temperature, then suction filtered to yield a solid product which was vacuum dried and recrystallized in petroleum ether to yield light yellow power crystal with a yield of 69.9%.
MS: M$^+$ 244.
$^1$H-NMR (CDCl$_3$, δ ppm): 2.78 (m, 2H), 2.92 (m, 2H), 3.85 (s, 3H), 5.41 (s, 1H), 6.14 (s, 1H), 6.47 (d, 1H), 6.54 (dd, 1H), 7.49 (d, 1H), 7.94 (t, 1H).

Example 17

Preparation of 2-methylene-5-(3,4-dimethoxybenzylidene)cyclopentanone

Step A Preparation of 2-(3,4-dimethoxybenzylidene)cyclopentanone

With reflux device installed, 36.8 g (0.24 mol) of N-cyclopentenyl morpholine, 0.20 mol of 3,4-dimethoxybenzaldehyde and 200 mL benzene were added to a round bottom flask and heated under reflux for 20 h. The resulting solution was cooled to 30° C. and slowly stirred while 62 mL of hydrochloric acid (6 mol/L) was added. After stirring for 2 h at room temperature, the benzene layer was separated and washed with water to neutral, and dried over anhydrous sodium sulfate overnight. Then the mixture was filtered to remove anhydrous sodium sulfate and benzene was recovered by evaporation under reduced pressure. The residue was cooled and solidified, then recrystallized in cyclohexane/ethanol to yield a light yellow flaky crystal product with a yield of 80.3%.

Step B Preparation of 2-(2,3-dimethoxybenzylidene)-5-dimethylaminomethyl-cyclopentanone hydrochloride 0.03 mol of 2-(2,3-dimethoxybenzylidene)cyclopentanone was dissolved in 30 mL anhydrous acetonitrile, treated with 8.4 g (0.09 mol) of N,N-dimethyl-methylene ammonium chloride under refluxing, refluxed for 12 h to yield a solid product which was then suction filtered, dried and recrystallized in acetonitrile/chloroform to yield 2-(3,4-dimethoxybenzylidene)-5-dimethylaminomethyl-cyclopentanone hydrochloride with a yield of 86.1%.

Step C Preparation of 2-methylene-5-(2,3-dimethoxybenzylidene)cyclopentanone 0.01 mol 2-(2,3-dimethoxybenzylidene)-5-dimethylaminomethyl cyclopentanone hydrochloride was dissolved in 50 mL distilled water, stirred for 72 h at room temperature, then suction filtered to yield a solid product which was vacuum dried and recrystallized in petroleum ether to yield light yellow power crystal with a yield of 71.0%.
MS: M$^+$ 244.
$^1$H-NMR (CDCl$_3$, δ ppm): 2.82 (m, 2H), 3.00 (m, 2H), 3.92 (s, 1H), 5.46 (s, 1H), 6.17 (s, 1H), 6.93 (d, 1H, J=8 Hz), 7.12 (s, 1H), 7.20 (d, 1H, J=8 Hz), 7.50 (s, 1H).

Example 18

Preparation of 2-methylene-5-(3,4-methylenedioxybenzylidene)cyclopentanone

Step A Preparation of 2-(3,4-dimethoxybenzylidene)cyclopentanone

With reflux device installed, 36.8 g (0.24 mol) of N-cyclopentenyl morpholine, 0.20 mol of 3,4-dimethoxybenzaldehyde and 200 mL benzene were added to a round bottom flask and heated under reflux for 20 h. The resulting solution was cooled to 30° C. and slowly stirred while 62 mL of hydrochloric acid (6 mol/L) was added. After stirring for 2 h at room temperature, the benzene layer was separated and washed with water to neutral, and dried over anhydrous sodium sulfate overnight. Then the mixture was filtered to remove anhydrous sodium sulfate and benzene was recovered by evaporation under reduced pressure. The residue was cooled and solidified, then recrystallized in cyclohexane/ethanol to yield a light yellow flaky crystal product with a yield of 69.3%.

Step B

Preparation of 2-(3,4-dimethoxybenzylidene)-5-(dimethylaminomethyl)-cyclopentanone hydrochloride 0.03 mol of 2-(3,4-dimethoxybenzylidene)cyclopentanone was dissolved in 30 mL anhydrous acetonitrile, treated with 8.4 g (0.09 mol) of N,N-dimethyl-methylene ammonium chloride under refluxing, refluxed for 12 h to yield a solid product which was then suction filtered, dried and recrystallized in acetonitrile/chloroform to yield 2-(3,4-dimethoxybenzylidene)-5-(dimethylaminomethyl)cyclopentanone hydrochloride with a recovery of 69.8%.

Step C

Preparation of 2-methylene-5-(3,4-dimethoxybenzylidene)cyclopentanone 0.01 mol 2-(2,4-dimethoxybenzylidene)-5-dimethylamino-methylcyclopentanone hydrochloride was dissolved in 50 mL distilled water, stirred for 72 h at room temperature, then suction filtered to yield a solid product which was vacuum dried and recrystallized in petroleum ether to yield light yellow power crystal with a recovery of 69.9%.

MS: M+ 228.

1H-NMR (CDCl$_3$, δ ppm): 2.83 (m, 2H), 2.95 (m, 2H), 5.45 (s, 1H), 6.02 (s, 2H), 6.17 (s, 1H), 6.87 (m, 1H), 7.08 (m, 2H), 7.46 (t, 1H).

Example 19

Preparation of 2-methylene-5-(3,5-dimethoxy-4-hydroxybenzylidene) cyclopentanone

Step A Preparation of 2-(3,5-dimethoxybenzylidene)cyclopentanone

With reflux device installed, 36.8 g (0.24 mol) of N-cyclopentenyl morpholine, 0.20 mol of 3,5-dimethoxybenzaldehyde and 200 mL benzene were added to a round bottom flask and heated under reflux for 20 h. The resulting solution was cooled to 30° C. and slowly stirred while 62 mL of hydrochloric acid (6 mol/L) was added. After stirring for 2 h at room temperature, the benzene layer was separated and washed with water to neutral, and dried over anhydrous sodium sulfate overnight. Then the mixture was filtered to remove anhydrous sodium sulfate and benzene was recovered by evaporation under reduced pressure. The residue was cooled and solidified, then recrystallized in cyclohexane/ethanol to yield a light yellow flaky crystal product with a yield of 79.9%.

Step B

Preparation of 2-(3,5-dimethoxybenzylidene)-5-dimethylamino-methyl cyclopentanone hydrochloride 0.03 mol of 2-(3,5-dimethoxybenzylidene)cyclopentanone was dissolved in 30 mL anhydrous acetonitrile, treated with 8.4 g (0.09 mol) of N,N-dimethyl-methylene ammonium chloride under refluxing, refluxed for 12 h to yield a solid product which was then suction filtered, dried and recrystallized in acetonitrile/chloroform to yield 2-(3,5-dimethoxy-benzylidene)-5-dimethylaminomethyl cyclopentanone hydrochloride with a yield of 89.3%.

Step C

Preparation of 2-methylene-5-(3,5-dimethoxybenzylidene)cyclopentanone 0.01 mol 2-(2,4-dimethoxybenzylidene)-5-dimethylamino-methyl-cyclopentanone hydrochloride was dissolved in 50 mL distilled water, stirred for 72 h at room temperature, then suction filtered to yield a solid product which was vacuum dried and recrystallized in petroleum ether to yield light yellow power crystal with a yield of 75.8%.

MS: [M+H] 261.

1H-NMR (CDCl$_3$, δ ppm): 2.83 (s, 2H), 2.30 (m, 2H), 3.94 (s, 6H), 5.47 (s, 1H), 5.80 (s, 1H), 6.18 (s, 1H), 6.85 (s, 2H), 7.47 (s, 1H).

Example 20

Preparation of 2-methylene-5-[3,5-di(t-butyl)-4-hydroxybenzylidene]-cyclopentanone

Step A: Preparation of 2-(3,5-di(t-butyl)-benzylidene)cyclopentanone

With reflux device installed, 36.8 g (0.24 mol) of N-cyclopentenyl morpholine, 0.20 mol of 3,5-di(t-butyl)-benzaldehyde and 200 mL benzene were added to a round bottom flask and heated under reflux for 20 h. The resulting solution was cooled to 30° C. and slowly stirred while 62 mL of hydrochloric acid (6 mol/L) was added. After stirring for 2 h at room temperature, the benzene layer was separated and washed with water to neutral, and dried over anhydrous sodium sulfate overnight. Then the mixture was filtered to remove anhydrous sodium sulfate and benzene was recovered by evaporation under reduced pressure. The residue was cooled and solidified, then recrystallized in cyclohexane/ethanol to yield a light yellow flaky crystal product with a yield of 86.9%.

Step B

Preparation of 2-(3,5-di(t-butyl)-benzylidene)-5-dimethylamino-methyl cyclopentanone hydrochloride 0.03 mol of 2-(3,5-di(t-butyl)-benzylidene)cyclopentanone was dissolved in 30 mL anhydrous acetonitrile, treated with 8.4 g (0.09 mol) of N,N-dimethyl-methylene ammonium chloride under refluxing, refluxed for 12 h to yield a solid product which was then suction filtered, dried and recrystallized in acetonitrile/chloroform to yield 2-(3,5-di(t-butyl)-benzylidene)-5-dimethylaminomethyl-cyclopentanone hydrochloride with a yield of 87.3%.

Step C

Preparation of 2-methylene-5-3,5-di(t-butyl)benzylidene)cyclopentanone 0.01 mol 2-(2,4-di(t-butyl)benzylidene)-5-dimethylamino-methyl-cyclopentanone hydrochloride was dissolved in 50 mL distilled water, stirred for 72 h at room temperature, then suction filtered to yield a solid product which was vacuum dried and recrystallized in petroleum ether to yield light yellow power crystal with a yield of 64.4%.

MS: M+ 312.

1H-NMR (CDCl$_3$, δ ppm): 1.46 (s, 18H), 2.83 (m, 2H), 2.97 (m, 2H), 5.44 (s, 1H), 5.57 (s, 1H), 6.15 (s, 1H), 7.46 (s, 2H), 7.54 (s, 1H)

Example 21

Preparation of 2-methylene-5-(3,4,5-trimethoxybenzylidene)cyclopentanone

Step A Preparation of 2-(3,4,5-trimethoxybenzylidene)cyclopentanone

With reflux device installed, 36.8 g (0.24 mol) of N-cyclopentenyl morpholine, 0.20 mol of 3,4,5-trimethoxybenzaldehyde and 200 mL benzene were added to a round bottom flask and heated under reflux for 20 h. The resulting solution was cooled to 30° C. and slowly stirred while 62 mL of hydrochloric acid (6 mol/L) was added. After stirring for 2 h at room temperature, the benzene layer was separated and washed with water to neutral, and dried over anhydrous sodium sulfate overnight. Then the mixture was filtered to remove anhydrous sodium sulfate and benzene was recovered by evaporation under reduced pressure. The residue was cooled and solidified, then recrystallized in cyclohexane/ethanol to yield a light yellow flaky crystal product with a yield of 80.2%.

Step B: Preparation of 2-(3,4,5-trimethoxyben-zylidene)-5-dimethylaminomethyl-cyclopentanone hydrochloride 0.03 mol of 2-(3,4,5-trimethoxybenzylidene)cyclopentanone was dissolved in 30 mL anhydrous acetonitrile, treated with 8.4 g (0.09 mol) of N,N-dimethyl-methylene ammonium chloride under refluxing, refluxed for 12 h to yield a solid product which was then suction filtered, dried and recrystallized in acetonitrile/chloroform to yield 2-(3,4,5-trimethoxy-benzylidene)-5-dimethylaminomethyl-cyclopentanone hydrochloride with a yield of 63.9%.

Step C Preparation of 2-methylene-5-(3,4,5-tri-methoxybenzylidene)cyclopentanone 0.01 mol 2-(3,4,5-trimethoxybenzylidene)-5-dimethylaminomethyl-cyclopentanone hydrochloride was dissolved in 50 mL distilled water, stirred for 72 h at room temperature, then suction filtered to yield a solid product which was vacuum dried and recrystallized in petroleum ether to yield light yellow power crystal with a yield of 69.7%.

MS: $M^+$ 274.
$^1$H-NMR (CDCl$_3$, δ ppm): 2.82 (s, 2H), 3.01 (m, 2H), 3.90 (s, 9H), 5.48 (s, 1H), 6.19 (s, 1H), 6.82 (s, 2H), 7.47 (s, 1H).

Example 22

Preparation of 2-methylene-5-(3-methylbutylidene)cyclopentanone

Step A: Preparation of 2-(3-methylbutylidene)cyclopentanone 1.88 g (0.047 mol) NaOH was dissolved in 83 mL of water, cooled to 5° C., and stirred in 8.56 g (0.102 mol) of cyclopetanone. After the temperature became stable, a mixture of 10.5 g (0.125 mol) cyclopentanone and 20.2 g (0.235 mol) of 3-methylbutaldehyde was added to the solution by drops with a controlled rate to keep the reaction temperature between 3~5° C., and after the drops, kept the reaction at this temperature for 2.5 h. 30 mL was then added for extraction and water layer was extracted with ether (30 mL×2). The ether extract was washed with saturated brine and dried over anhydrous magnesium sulfate. Then it was concentrated and distillated under reduced pressure, and the fraction of 136~138° C./2000 Pa was collected, which yielded 25.0 g of the product with a yield of 70%.

Following the same steps B and C as mentioned in EXAMPLE 1, a light yellow oily product as the final product was obtained.

MS: $M^+$ 164.
$^1$H-NMR (CDCl$_3$, δ ppm): 0.96 (d, 6H), 1.80 (m, 1H), 2.08 (m, 2H), 2.59 (m, 2H), 2.71 (m, 2H), 5.40 (s, 1H), 6.10 (s, 1H), 6.74 (s, 1H).

Example 23

Preparation of 2-methylene-5-(4-hydroxybenzylidene)cyclopentanone

Step A: Preparation of 2-(4-hydroxybenzylidene)cyclopentanone

A mixture of 26.5 g (0.22 mol) of p-hydroxybenzaldehyde and 53.0 g (0.63 mol) of cyclopetanone was added with 21 mL anhydrous piperidine under agitation to give a brownish red solution with heat emission. The solution was cooled to room temperature and stirred for 12 h. 200 mL of water was added to the resulting solution and treated with diluted acetic acid to adjust the pH value to 6. Then 20 mL toluene was added to the solution, stirred for 1 h, and suction filtered to yield a yellow solid product which was washed with diluted hydrochloric acid followed by water. Finally, it was dried and recrystallized in ethanol/water (1:1) to yield 23.0 g of yellow solid with a yield of 55.6%.

Following the same steps B and C as mentioned in EXAMPLE 1, a light yellow flaky crystal as the final product was obtained.

MS: $M^+$ 200.
$^1$H-NMR (CDCl$_3$, δ ppm): 2.83 (m, 2H), 2.97 (m, 2H), 5.47 (s, 1H), 5.66 (s, 1H), 6.18 (s, 1H), 6.90 (m, 2H), 7.50 (m, 3H).

Example 24

Preparation of 2-methylene-5-(2-hydroxybenzylidene)cyclopentanone

Step A: Preparation of 2-(2-hydroxybenzylidene)cyclopentanone

A mixture of 26.5 g (0.22 mol) of 2-hydroxybenzaldehyde and 53.0 g (0.63 mol) of cyclopetanone was added with 21 mL anhydrous piperidine under agitation to give a brownish red solution with heat emission. The solution was cooled to room temperature and stirred for 12 h. 200 mL of water was added to the resulting solution and treated with diluted acetic acid to adjust the pH value to 6. Then 20 mL toluene was added to the solution, stirred for 1 h, and suction filtered to yield a yellow solid product which was washed with diluted hydrochloric acid followed by water. Finally, it was dried and recrystallized in ethanol/water (1:1) to yield a yellow solid product with a yield of 67.8%.

Following the same steps B and C as mentioned in EXAMPLE 1, a light yellow flaky crystal as the desired final product was obtained with a yield of 65.4%.

MS: $M^+$ 200.
$^1$H-NMR (CDCl$_3$, δ ppm): 2.80 (t, 2H), 2.94 (t, 2H), 5.49 (s, 1H), 6.21 (m, 2H), 6.94 (m, 2H), 7.48 (d, 1H), 8.02 (s, 1H).

Example 25

Preparation of 2-methylene-5-diphenylmethylenecyclopentanone

Step A: Preparation of cyclopentanone-2-carboxylic acid ethyl ester 15.0 g (0.652 mmol) of sodium was placed in 150 mL toluene, heated to reflux, shaken, and made into sodium sand. 81.6 g (0.400 mol) of diethyl adipate was added in drops to the mixture in an outside bath at 105-110° C., and the resultant solution changed into a yellow sticky product. After refluxing for 8 h, the solution was cooled by ice bath, and 400 mL of 10% acetic acid solution was added in drops. The mixture was suction filtered and washed with a small amount of toluene. The filtrate was separated into layers. The upper layer was washed with 7% sodium carbonate (260 mL×2) followed by saturated brine (200 mL×2), and dried overnight with anhydrous magnesium sulfate. The solution was filtered, concentrated and distilled under reduced pressure to collect the fractions of bp: 142-150° C./2660 Pa, yielding 53.3 g of colorless liquid with a yield of 85.6%.

Step B: Preparation of ethyl 2-ethylenedioxy-cyclopentane carboxylate 7.6 g (0.049 mol) cyclopentanone-2-carboxylic acid, 6.0 g (0.098 mol) ethylene alcohol, 0.05 g p-toluene sulfonic acid and 50 mL benzene were refluxed with water segregator for 44 h. The solution was diluted with 20 mL benzene, washed with distilled water, 7% sodium carbonate, and distilled water to pH 7, successively, then dried overnight with anhydrous magnesium sulfate. After removal of most of the solvent, the solution was filtered, concentrated and distilled under reduced pressure to collect the fractions of bp: 141-146° C./2660 Pa, yielding 5.51 g of colorless liquid with a yield of 55.2%.

Step C: Preparation of 2-diphenylmethylene-cyclopentanone 6.51 g (0.268 mol) of magnesium scraps, an iodine pellet, and one-third of 40.8 g (0.257 mol) of bromobenzene in 100 mL of absolute ether solution were added to a three-necked bottle. After heating under reflux, the color of iodine faded gradually. After agitation, the remaining bromobenzene in absolute ether solution was added over 40 min, and the refluxing of the mixture was continued for 60 min. Then 21.4 g (0.105 mol) of 2-ethylendioxy-cyclopentane carboxylic acid ethyl ester in 50 mL of absolute ether solution was added in drops over about 35 min, and the refluxing of the mixture was continued for 60 min. The mixture was cooled and added in drops with 156 mL of 37% (w/v) ammonium chloride solution under stirring. The resulting solution was suction filtrated and separated into layers, and the water layer was extracted with ether, and the collected organic phases were pooled. After removal of the solvent, 62 mL methanol, 43 mL water and 3.1 mL concentrated hydrochloric acid were added, and the solution was refluxed for 5 h under violent stirring. After cooling at low temperature, the solution was suction filtrated, dried and recrystallized with anhydrous ethanol to yield 7.43 g of yellow flaky crystal with a yield of 28.5%, and the melting point of the product was determined to be 114-115° C.

Following the same steps B and C as mentioned in EXAMPLE 1, a light yellow flaky crystal as the final product was obtained with a yield of 72%.

MS: $M^+$ 260.

$^1$H-NMR (CDCl$_3$, δ ppm): 2.70 (m, 2H), 2.85 (m, 2H), 5.39 (s, 1H), 6.03 (s, 1H), 7.17 (m, 2H), 7.24 (m, 2H), 7.35 (m, 6H).

Example 26

Preparation of 2-methylene-5-[bis(4-methylphenyl)-methylene]cyclopentanone

Step A: Preparation of 2-(4-methylbenzylidene)cyclopentanone 6.51 g (0.268 mol) of magnesium scraps, an iodine pellet, one-third of 0.257 mol of 4-methylbromobenzene in 100 mL of absolute ether solution were added to a three-necked bottle. After heating under reflux, the color of iodine faded gradually. After agitation, the remaining bromobenzene in absolute ether solution was added over 40 min, and the refluxing of the mixture was continued for 60 min. Then 21.4 g (0.105 mol) of 2-ethylendioxy-cyclopentane carboxylic acid ethyl ester in 50 mL of absolute ether solution was added in drops over about 35 min, and the refluxing of the mixture was continued for 60 min. The mixture was cooled and added in drops with 156 mL of 37% (w/v) ammonium chloride solution under stirring. The resulting solution was suction filtrated and separated into layers, and the water layer was extracted with ether, and the collected organic phases were pooled. After removal of the solvent, 62 mL methanol, 43 mL water and 3.1 mL concentrated hydrochloric acid were added, and the solution was refluxed for 5 h under violent stirring. After cooling at low temperature, the solution was suction filtrated, dried and recrystallized with anhydrous ethanol to yield 7.43 g of yellow flaky crystal with a yield of 35.1%.

Following the same steps B and C as mentioned in EXAMPLE 1, a light yellow flaky crystal as the desired final product was obtained with a yield of 70%.

MS: $M^+$ 288.

$^1$H-NMR (CDCl$_3$, δ ppm): 2.36 (s, 6H), 2.67 (t, 2H), 2.82 (t, 2H), 5.35 (s, 1H), 5.99 (s, 1H), 7.02 (d, 2H, J=8 Hz), 7.09 (d, 2H, J=8 Hz), 7.13 (t, 4H).

Example 27

Preparation of 2-methene-5-[bis(4-fluorophenyl)-methylene]cyclopentanone

Step A Preparation of 2-(4-fluorobenzylidene)cyclopentanone 6.51 g (0.268 mol) of magnesium scrap, an iodine pellet, one-third of 0.257 mol of 4-fluorobromobenzene in 100 mL of absolute ether solution were added to a three-necked bottle. After heating under reflux, the color of iodine faded gradually.

After agitation, the remaining bromobenzene in absolute ether solution was added over 40 min, and the refluxing of the mixture was continued for 60 min. Then 21.4 g (0.105 mol) of 2-ethylendioxy-cyclopentane carboxylic acid ethyl ester in 50 mL of absolute ether solution was added in drops over about 35 min, and the refluxing of the mixture was continued for 60 min. The mixture was cooled and added in drops with 156 mL of 37% (w/v) ammonium chloride solution under stirring. The resulting solution was suction filtrated and separated into layers, and the water layer was extracted with ether, and the collected organic phases were pooled. After removal of the solvent, 62 mL methanol, 43 mL water and 3.1 mL concentrated hydrochloric acid were added, and the solution was refluxed for 5 h under violent stirring. After cooling at low temperature, the solution was suction filtrated, dried and recrystallized with anhydrous ethanol to yield a yellow flaky crystal with a yield of 42.3%.

Following the same steps B and C as mentioned in EXAMPLE 1, a light yellow flaky crystal was obtained as the desired final product with a yield of 63.3%.

MS: $M^+$ 297.

$^1$H-NMR (CDCl$_3$, δ ppm): 2.71 (t, 2H), 2.82 (t, 2H), 5.41 (s, 1H), 6.04 (s, 1H), 7.05 (m, 4H), 7.11 (t, 1H), 7.19 (t, 2H).

Example 28

Preparation of 2-methene-5-[(E)-3-phenylallylidene]cyclopentanone

Step A: Preparation of 2-[(E)-3-phenylallylidene]cyclopentanone 20 mL of 15% sodium hydroxide was diluted with distilled water to 700 mL, then the reaction system was added with a mixture of 8.4 g (0.1 mol) of cyclopentanone and 6.6 g (0.05 mol) of cinnamaldehyde. The mixture was stirred for 48 h at room temperature, and added dropwise with 5% hydrochloric acid to neutralize the pH value to pH=6-7 under a cooling condition. The resulting mixture was then suction filtrated to yield a yellow solid product which was crystallized by with cyclohexane to yield 7.9 g of solid yellow power with a yield of 80.0%, and the melting point of the product was determined to be 117-118° C.

Following the same steps B and C as mentioned in EXAMPLE 1, a light yellow flaky crystal as the desired final product was obtained with a yield of 70%.

MS: M+ 210.

$^1$H-NMR (CDCl$_3$, δ ppm): 2.77 (m, 2H), 2.87 (m, 2H), 5.51 (s, 1H), 5.95 (s, 1H), 7.19 (m, 3H), 7.42 (m, 3H), 7.68 (m, 2H).

Example 29

Preparation of 2-methylene-5-[(E)-2-methyl-3-phenylallylidene]cyclopentanone

Step A: Preparation of 2-methyl-3-phenylacrylaldehyde 13.78 g (0.13 mol) of benzaldehyde, 5 g of KF—Al$_2$O$_3$ and 5 mL of PEG-400 were added to a 250 mL three-necked flask. At 30° C., 5.80 g (0.10 mol) of n-propionaldehyde was added dropwise to the mixture while stirring, and reacted under the controlled dropping speed. After 4 h, the solution was transferred into a separating funnel, and the organic phase was collected, washed with saturated brine to neutral, and dried over anhydrous magnesium sulfate. After removal of most of the solvent, the solution was concentrated and distilled under reduced pressure. The fractions of bp: 130-132° C./2660 Pa was collected to yield 12.30 g of light yellow liquid product with a yield of 89.0%.

Following the same steps B and C as mentioned in EXAMPLE 28, a light yellow flaky crystal as the desired final product was obtained with a yield of 66%.

MS: M+ 224.

$^1$H-NMR (CDCl$_3$, δ ppm): 2.18 (s, 3H, —CH$_3$), 2.70 (m, 2H), 2.99 (m, 2H), 5.47 (s, 1H), 5.93 (s, 1H), 7.06 (d, 2H, J=13.2 Hz), 7.30 (d, 1H, J=3.9 Hz), 7.40 (m, 4H).

Example 30

Pharmacological Study on the Products of the Invention

In Vitro Antitumor Activity Test
1) Cell Thawing

Cells were taken out carefully from liquid nitrogen (Frozen pipes), and the cell freezing medium was thawed rapidly in water bath at 37° C. in order to rapidly pass the temperature range of 0~5° C. within which the cell is easily damaged. Cell suspension was sucked with pipette gun and put it into centrifuge tubes under a sterile condition, then centrifuged for 3 min at 1300 r/min. The supernatant was gently discarded, and then added with a fresh medium to pipette and mix the cells. Finally, the cells were transferred into culture flasks and cultured in a carbon dioxide incubator. The medium was changed once after 24 h.

2) Cell Culture

Human prostate cancer cells (DU145, PC-3) were cultured in RPMI1640 medium containing 10% fetal bovine serum inactivated by heating, 100 IU/mL penicillin, 100 μg/mL streptomycin and 1 mmol/L L-glutamine. Human breast cancer cells (T47D, MDA-MB231) were cultured in RPMI1640 medium containing 10% fetal bovine serum inactivated by heating, 5 μg/mL insulin, 100 IU/mL penicillin, 100 μg/mL streptomycin, and 1 mmol/L L-glutamine. Human breast cancer cells (MCF-7) were cultured in DMEM culture medium containing 10% fetal bovine serum inactivated by heating, 5 μg/mL insulin, 100 IU/mL penicillin, 100 μg/mL streptomycin and 1 mol/L L-glutamine. Mouse Lewis lung carcinoma cells (LL/2) and mouse melanoma cells (B16F0) were cultured in DMEM culture medium containing 10% fetal bovine serum inactivated by heating, 4.5 g/L glucose, 1.5 g/L NaHCO$_3$, 100 IU/mL penicillin, 100 μg/mL streptomycin and 4 mmol/L L-glutamine. All of the above cell lines were incubated in 37° C. incubator with 5% carbon dioxide saturated humidity 3) Cell Passage After 2-3 cycles of cell culture and passage after the cell thawing, the cells were stable and ready for the experiment. The flask bottom should be covered with cells in each cell passage.

4) Cell Coated Plate

Trypsin solution (0.25%) was applied to digest the cells off the flask bottom when the flask bottom was covered with cells. The digested cell solution was moved to the centrifuge tubes and culture medium was added to stop the digestion; centrifuged for 3 min at 1300 r/min conditions; gently discarded the supernatant, and then added 5 mL medium, pipetted and mixed the cells; added 10 μL of the cell suspension to the cell count plate to count; adjusted the cell concentration to 2×10$^4$/mL; added 100 μL cell suspension to all wells of the 96 well plate except A1 well which acts as a blank; and placed the 96 well plate in an incubator to culture 24 h and to make sure the cells growing and attached on the wells.

5) Administration to Cell

First formulated the medicine in 16 mmol/L of DMSO storage solution; then diluted the solution with ethanol to 1.6 mmol/L solution; then further diluted with cell culture medium to 32 μmol/L, 16 μmol/L, 8 μmol/L, 4 μmol/L, 2 μmol/L and 1 μmol/L, and added to 96 well plate; 100 μl drug solution were added to each well, thus the final drug concentrations of cells were 16 μmol/L, 8 μmol/L, 4 μmol/L, 2 μmol/L, 1 μmol/L, and 0.5 μmol/L; 3 parallel wells were set for each concentration and placed the 96 well plate was placed into an incubator to continuously culture for 4 days 6) Investigation of the Cell Growth Inhibition Activity of Compounds by MTT Added to each well of the 96 well plate with 50 μL of MTT (2 mg/mL); discarded the MTT (tetrazolium) solution after 4 h incubation in an incubator, then added 200 μL of DMSO; shaking the 96 well plate in a magnetic shaker for 10 min to make sure that the reaction product of the living cells and the MTT, i.e. formazan, was fully dissolved; measured the absorbance value (OD) in microplate reader at the selected 570 nm wavelength, and recorded results. Using the OD values of the cells that were not added with drugs as control, the cell growth inhibition ratio at each test concentration was calculated by using the following formula. Herein, the cancer cell growth inhibition is expressed as the half of the growth inhibitory concentration (IG$_{50}$ Value) (i.e., the tested drug concentration resulting in 50% cell growth inhibition). Cell growth inhibition rate (%)=(1−OD value of cell group with drug/OD value of control group without drug)×100%

OD value of cell group with drug is the OD value measured by adding drugs to a well; OD value of control group without drug is the OD value measured without drugs.

7) The Results of the Growth Inhibitory Activity of the Compounds on Human Breast Cancer Cells T47D and MDA-MB231 were Listed in Table 1.

TABLE 1

The IC$_{50}$ (μmol/L) value list of the compounds on the T47D and MDA-MB231

| Example No. | IC$_{50}$ (μmol/L) | |
| --- | --- | --- |
| | T47D | MDA-MB231 |
| Example 2 | >16 | >16 |
| Example 7 | 3.93 | 11.58 |
| Example 8 | 6.37 | 4.57 |
| Example 9 | >16 | >16 |
| Example 10 | 1.64 | 4.96 |
| Example 11 | 1.40 | 8.58 |
| Example 12 | 1.29 | 4.68 |
| Example 13 | 0.64 | 2.53 |
| Example 14 | 0.98 | 3.21 |
| Example 15 | >16 | >16 |
| Example 16 | >16 | 7.51 |
| Example 17 | 2.66 | 2.57 |
| Example 18 | 4.89 | 6.68 |
| Example 19 | 2.82 | 3.44 |
| Example 20 | 5.31 | 14.84 |
| Example 21 | 2.76 | 7.84 |
| Example 22 | >16 | >16 |
| Example 23 | >16 | 5.96 |
| Example 24 | 5.02 | 5.54 |
| Example 25 | 7.23 | >16 |
| Example 26 | 4.36 | 7.49 |
| Example 27 | 16.08 | >16 |
| WB852 | 4.55 | 3.26 |

8) The Results of the Growth Inhibitory Activity of the Compounds on Human Breast Cancer Cells MCF-7, Human Prostate Cancer Cells DU145, PC-3, Mouse Lewis Lung Cancer Cell LL/2, and Mouse Melanoma Cells B16F0 were Listed in Table 2.

TABLE 2

| Example No. | IC$_{50}$ (μmol/L) | | | | |
| --- | --- | --- | --- | --- | --- |
| | PC-3 | MCF-7 | DU145 | LL/2 | B16FD |
| Example 13 | 2.01 | 1.21 | 2.95 | 5.09 | 3.42 |
| Example 14 | 1.76 | 1.05 | 2.43 | 6.39 | 4.40 |

9) Acute Toxicity Test

Animals: healthy Kunming mice, half male and half female, weighed 18-22 g. Animals were provided from Experimental Animal Center of Shenyang Pharmaceutical University. Certificate of Conformity: Real co-Zi Liao No. 033

Name of tested drugs: Example 13, Example 14

Drug preparation: Suspension formulated with 0.2% polysorbate 80 (Tween-80). Dosage to subject is expressed as mg/kg.

Route of administration: Intraperitoneal injection; injection volume was 0.1 ml/10 g, with one time multi-dose administration.

Test cycle and measurement: Observed one week after the administration; recorded toxic reactions in mice daily during observation, with the death of mice as the main indicator. Half lethal dose (LD$_{50}$, mg/kg) of the administration of compound after a week can be obtained according to weighted regression method.

10) Results of Acute Toxicity Test of Example 13 and Example 14 were Listed in Table 3.

TABLE 3

List of the compound LD$_{50}$ (mg/kg) values

| Example No. | LD$_{50}$ (mg/kg) | LD$_{50}$, 95% confidence interval (mg/kg) |
| --- | --- | --- |
| Example 13 | 22.4 | 14.5-38.4 |
| Example 14 | 35.2 | 21.5-52.6 |

What is claimed is:

1. 2-methylene-5-substituted-methylenecyclopentanone derivatives, wherein the 2-methylene-5-substituted-methylenecyclopentanone derivatives having the formula:

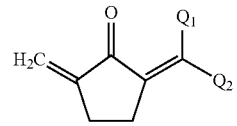

I wherein Q$_1$ is hydrogen, Q$_2$ is a straight or branched C1-C10 alkyl, C3-C7 cycloalkyl, or 5 to 10 membered heterocyclic group; wherein the heterocyclic group may contain 1 to 4 heteroatom selected from nitrogen, oxygen and sulfur, and optionally contains 1 or 2 carbon-carbon double bond or triple bond; wherein the heterocyclic group may be optionally substituted with 1 to 5 same or different R$_1$, wherein R$_1$ is independently selected from hydroxyl, halogen, nitro, cyano, carbonyl, trifluoromethyl, trifluoromethoxy, C1-C4 alkyl, C1-C4 alkoxylmethyl, C1-C4 alkoxyl, N,N-di-C1-C4 alkylamino or C3-C7 cycloalkyl; and wherein cycloalkyl may contain 1 or 2 carbon-carbon double bond or triple bond;

wherein Q$_1$ is hydrogen, Q$_2$ is substituted C6-C10 aryl, wherein aryl may be optionally substituted with 1 to 5 same or different R$_2$; wherein R$_2$ is independently selected from hydroxyl, halogen, carboxyl, amino, nitro, cyano, trifluoromethyl, trifluoromethoxy, C1-C4 alkyl, C3-C7 cycloalkyl, C1-C4 alkoxyl, C1-C3 alkylene dioxy, C1-C4 alkoxylmethyl, amino substituted with mono- or di-C1-C4 alkyl, C1-C4 alkylsulphonyl, or benzoyloxy substituted with R$_1$;

wherein Q$_1$ is hydrogen, Q$_2$ is

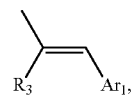

wherein R$_3$ is independently selected from hydroxyl, halogen, and C1-C4 alkyl; Ar$_1$ is C6-C10 aryl or 5 to 10 membered heteroaryl; wherein heteroaryl may contain 1 to 4 heteratoms selected from nitrogen, oxygen, or sulfur atoms; wherein aryl may be optionally substituted with 1 to 5 same or different R$_1$; or Q$_1$ and Q$_2$ are the same or different substituted C6-C10 aryl, wherein aryl may be optionally substituted with 1 to 5 same or different R$_4$; R$_4$ is independently selected from halogen, nitro, cyano, haloalkyl, C1-C4 alkyl or C1-C4 alkoxyl, wherein the 2-methylene-5-substituted-methylenecyclopentanone derivative is not 2-methylene-5-(4-methoxybenzylidene)cyclopentanone.

2. The 2-methylene-5-substituted-methylenecyclopentanone derivatives according to claim 1, wherein $Q_1$ is hydrogen, $Q_2$ is straight or branched C1-C10 alkyl, or C3-C7 cycloalkyl; wherein the cycloalkyl may contain 1 to 2 carbon-carbon double bond or triple bond.

3. The 2-methylene-5-substituted-methylenecyclopentanone derivatives according to claim 1, wherein $Q_1$ is hydrogen, $Q_2$ is phenyl or phenyl group optionally substituted with one to five same or different $R_2$; wherein $R_2$ is independently selected from hydroxyl, halogen, carboxyl, amino, nitro, cyano, trifluoromethyl, trifluoromethoxy, C1-C4 alkyl, C3-C7 cycloalkyl, C1-C4 alkoxyl, C1-C3 alkylene dioxy, C1-C4 alkoxylmethyl, amino substituted with mono- or di-C1-C4 alkyl, C1-C4 alkylsulphonyl, or benzoyloxy substituted with $R_1$.

4. The 2-methylene-5-substituted-methylenecyclopentanone derivatives according to claim 1, where $Q_1$ is hydrogen, $Q_2$ is

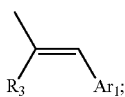

wherein $R_3$ is independently selected from hydrogen and C1-C4 alkyl;
$Ar_1$ is phenyl, or phenyl group optionally substituted with 1 to 5 same or different $R_2$; wherein $R_2$ is independently selected from hydroxyl, halogen, carboxyl, amino, nitro, cyano, trifluoromethyl, trifluoromethoxy, C1-C4 alkyl, C3-C7 cycloalkyl, C1-C4 alkoxyl, C1-C3 alkylene dioxy, C1-C4 alkoxylmethyl, amino substituted with mono- or di-C1-C4 alkyl, C1-C4 alkylsulphonyl or benzoyloxy substituted with $R_1$.

5. The 2-methylene-5-substituted-methylenecyclopentanone derivatives according to claim 1, wherein
$Q_1$ and $Q_2$ are phenyl, or different phenyl group optionally substituted with 1 to 5 same or different $R_4$; wherein $R_4$ is independently selected from halogen, C1-C4 alkyl, or C1-C4 alkoxyl.

6. The 2-methylene-5-substituted-methylenecyclopentanone derivatives according to claim 1, wherein the 2-methylene-5-substituted-methylenecyclopentanone derivatives are selected from the group consisting of:
2-methylene-5-(4-chlorobenzylidene)cyclopentanone,
2-methylene-5-benzylidene-cyclopentanone,
2-methylene-5-(4-methylbenzylidene)cyclopentanone,
2-methylene-5-(3-methoxybenzylidene)cyclopentanone,
2-methylene-5-(4-bromobenzylidene)cyclopentanone,
2-methylene-5-(2-methoxybenzylidene)cyclopentanone,
2-methylene-5-(4-ethoxybenzylidene)cyclopentanone,
2-methylene-5-(4-propoxybenzylidene)cyclopentanone,
2-methylene-5-(4-methanesulfonylbenzylidene)cyclopentanone,
2-methylene-5-(4-N,N-dimethylbenzylidene)cyclopentanone,
2-methylene-5-(2-hydroxy-4-methoxybenzylidene)cyclopentanone,
2-methylene-5-(3-hydroxy-4-methoxybenzylidene)cyclopentanone,
2-methylene-5-(3-methoxy-4-hydroxybenzylidene)cyclopentanone,
2-methylene-5-(2,3-dimethoxybenzylidene)cyclopentanone,
2-methylene-5-(2,4-dimethoxybenzylidene)cyclopentanone,
2-methylene-5-(3,4-dimethoxybenzylidene)cyclopentanone,
2-methylene-5-(3,4-methylenedioxy-benzylidene)cyclopentanone,
2-methylene-5-(3,5-dimethoxy-4-hydroxybenzylidene)cyclopentanone,
2-methylene-5-(3,5-di(t-butyl)-4-hydroxybenzylidene)cyclopentanone,
2-methylene-5-(3,4,5-trimethoxybenzylidene)cyclopentanone,
2-methylene-5-(3-methylbutylidene)cyclopentanone,
2-methylene-5-(4-hydroxybenzylidene)cyclopentanone,
2-methylene-5-(2-hydroxybenzylidene)cyclopentanone,
2-methylene-5-diphenylmethylenecyclopentanone,
2-methylene-5-[bis(4-methylphenyl)-methylene]cyclopentanone,
2-methylene-5-[bis(4-fluorophenyl)-methylene]cyclopentanone,
2-methylene-5-[(E)-3-phenylallylidene]cyclopentanone, and
2-methylene-5-(E)-2-methyl-3-phenylallylidene)cyclopentanone.

7. A pharmaceutical composition, comprising a pharmaceutically acceptable carrier and/or adjuvant, and a compound of the formula:

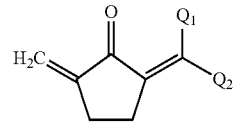

wherein $Q_1$ is hydrogen, $Q_2$ is a straight or branched C1-C10 alkyl, C3-C7 cycloalkyl, or 5 to 10 membered heterocyclic group; wherein the heterocyclic group may contain 1 to 4 heteroatom selected from nitrogen, oxygen and sulfur, and optionally contains 1 or 2 carbon-carbon double bond or triple bond; wherein the heterocyclic group may be optionally substituted with 1 to 5 same or different $R_1$, wherein $R_1$ is independently selected from hydroxyl, halogen, nitro, cyano, carbonyl, trifluoromethyl, trifluoromethoxy, C1-C4 alkyl, C1-C4 alkoxylmethyl, C1-C4 alkoxyl, N,N-di-C1-C4 alkylamino or C3-C7 cycloalkyl; and wherein cycloalkyl may contain 1 or 2 carbon-carbon double bond or triple bond;
wherein $Q_1$ is hydrogen, $Q_2$ is substituted C6-C10 aryl, wherein aryl may be optionally substituted with 1 to 5 same or different $R_2$; wherein $R_2$ is independently selected from hydroxyl, halogen, carboxyl, amino, nitro, cyano, trifluoromethyl, trifluoromethoxy, C1-C4 alkyl, C3-C7 cycloalkyl, C1-C4 alkoxyl, C1-C3 alkylene dioxy, C1-C4 alkoxylmethyl, amino substituted with mono- or di-C1-C4 alkyl, C1-C4 alkylsulphonyl, or benzoyloxy substituted with $R_1$;
wherein $Q_1$ is hydrogen, $Q_2$ is

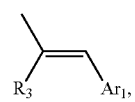

wherein $R_3$ is independently selected from hydroxyl, halogen, and C1-C4 alkyl; $Ar_1$ is C6-C10 aryl or 5 to 10 membered heteroaryl; wherein heteroaryl may contain 1 to 4 heteroatoms selected from nitrogen, oxygen, or sulfur atoms; wherein aryl may be optionally substituted with 1 to 5 same or different $R_1$; or Q$_1$ and Q$_2$ are the same or different substituted C6-C10 aryl, wherein aryl may be optionally substituted with 1 to 5 same or different $R_4$; $R_4$ is independently selected from halogen, nitro, cyano, haloalkyl, C1-C4 alkyl or C1-C4 alkoxyl.

8. The pharmaceutical composition of claim 7 wherein $Q_1$ is hydrogen, $Q_2$ is straight or branched C1-C10 alkyl, or C3-C7 cycloalkyl; wherein the cycloalkyl may contain 1 to 2 carbon-carbon double bond or triple bond.

9. The pharmaceutical composition of claim 7, wherein $Q_1$ is hydrogen, $Q_2$ is phenyl or phenyl group optionally substituted with one to five same or different $R_2$; wherein $R_2$ is independently selected from hydroxyl, halogen, carboxyl, amino, nitro, cyano, trifluoromethyl, trifluoromethoxy, C1-C4 alkyl, C3-C7 cycloalkyl, C1-C4 alkoxyl, C1-C3 alkylene dioxy, C1-C4 alkoxylmethyl, amino substituted with mono- or di-C1-C4 alkyl, C1-C4 alkylsulphonyl, or benzoyloxy substituted with $R_1$.

10. The pharmaceutical composition of claim 7, where $Q_1$ is hydrogen, $Q_2$ is

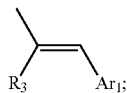

wherein $R_3$ is independently selected from hydrogen and C1-C4 alkyl;

Ar$_1$ is phenyl, or phenyl group optionally substituted with 1 to 5 same or different $R_2$; wherein $R_2$ is independently selected from hydroxyl, halogen, carboxyl, amino, nitro, cyano, trifluoromethyl, trifluoromethoxy, C1-C4 alkyl, C3-C7 cycloalkyl, C1-C4 alkoxyl, C1-C3 alkylene dioxy, C1-C4 alkoxylmethyl, amino substituted with mono- or di-C1-C4 alkyl, C1-C4 alkylsulphonyl or benzoyloxy substituted with $R_1$.

11. The pharmaceutical composition of claim 7, wherein $Q_1$ and $Q_2$ are phenyl, or different phenyl group optionally substituted with 1 to 5 same or different $R_4$; wherein $R_4$ is independently selected from halogen, C1-C4 alkyl, or C1-C4 alkoxyl.

12. The pharmaceutical composition of claim 7, wherein the compound is selected from the group consisting of:
2-methylene-5-(4-chlorobenzylidene)cyclopentanone,
2-methylene-5-(4-methoxybenzylidene)cyclopentanone,
2-methylene-5-benzylidene-cyclopentanone,
2-methylene-5-(4-methylbenzylidene)cyclopentanone,
2-methylene-5-(3-methoxybenzylidene)cyclopentanone,
2-methylene-5-(4-bromobenzylidene)cyclopentanone,
2-methylene-5-(2-methoxybenzylidene)cyclopentanone,
2-methylene-5-(4-ethoxybenzylidene)cyclopentanone,
2-methylene-5-(4-propoxybenzylidene)cyclopentanone,
2-methylene-5-(4-methanesulfonylbenzylidene)cyclopentanone,
2-methylene-5-(4-N,N-dimethylbenzylidene)cyclopentanone,
2-methylene-5-(2-hydroxy-4-methoxybenzylidene)cyclopentanone,
2-methylene-5-(3-hydroxy-4-methoxybenzylidene)cyclopentanone,
2-methylene-5-(3-methoxy-4-hydroxybenzylidene)cyclopentanone,
2-methylene-5-(2,3-dimethoxybenzylidene)cyclopentanone,
2-methylene-5-(2,4-dimethoxybenzylidene)cyclopentanone,
2-methylene-5-(3,4-dimethoxybenzylidene)cyclopentanone,
2-methylene-5-(3,4-methylenedioxy-benzylidene)cyclopentanone,
2-methylene-5-(3,5-dimethoxy-4-hydroxybenzylidene)cyclopentanone,
2-methylene-5-(3,5-di(t-butyl)-4-hydroxybenzylidene)cyclopentanone,
2-methylene-5-(3,4,5-trimethoxybenzylidene)cyclopentanone,
2-methylene-5-(3-methylbutylidene)cyclopentanone,
2-methylene-5-(4-hydroxybenzylidene)cyclopentanone,
2-methylene-5-(2-hydroxybenzylidene)cyclopentanone,
2-methylene-5-diphenylmethylenecyclopentanone,
2-methylene-5-[bis(4-methylphenyl)-methylene]cyclopentanone,
2-methylene-5-[bis(4-fluorophenyl)-methylene]cyclopentanone,
2-methylene-5-[(E)-3-phenylallylidene]cyclopentanone, and
2-methylene-5-(E)-2-methyl-3-phenylallylidene)cyclopentanone.

13. A method for treating cancer comprising administering to a subject in need thereof a therapeutically effective amount of a pharmaceutical composition comprising a pharmaceutically acceptable carrier and/or adjuvant, and a compound of the formula:

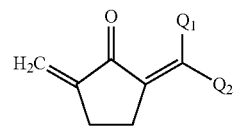

wherein $Q_1$ is hydrogen, $Q_2$ is a straight or branched C1-C10 alkyl, C3-C7 cycloalkyl, or 5 to 10 membered heterocyclic group; wherein the heterocyclic group may contain 1 to 4 heteroatom selected from nitrogen, oxygen and sulfur, and optionally contains 1 or 2 carbon-carbon double bond or triple bond; wherein the heterocyclic group may be optionally substituted with 1 to 5 same or different $R_1$, wherein $R_1$ is independently selected from hydroxyl, halogen, nitro, cyano, carbonyl, trifluoromethyl, trifluoromethoxy, C1-C4 alkyl, C1-C4 alkoxylmethyl, C1-C4 alkoxyl, N,N-di-C1-C4 alkylamino or C3-C7 cycloalkyl; and wherein cycloalkyl may contain 1 or 2 carbon-carbon double bond or triple bond;

wherein $Q_1$ is hydrogen, $Q_2$ is substituted C6-C10 aryl, wherein aryl may be optionally substituted with 1 to 5 same or different $R_2$; wherein $R_2$ is independently selected from hydroxyl, halogen, carboxyl, amino, nitro, cyano, trifluoromethyl, trifluoromethoxy, C1-C4 alkyl, C3-C7 cycloalkyl, C1-C4 alkoxyl, C1-C3 alkylene dioxy, C1-C4 alkoxylmethyl, amino substituted with mono- or di-C1-C4 alkyl, C1-C4 alkylsulphonyl, or benzoyloxy substituted with $R_1$;

wherein $Q_1$ is hydrogen, $Q_2$ is

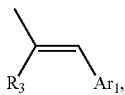

wherein $R_3$ is independently selected from hydroxyl, halogen, and C1-C4 alkyl; $Ar_1$ is C6-C10 aryl or 5 to 10 membered heteroaryl; wherein heteroaryl may contain 1 to 4 heteratoms selected from nitrogen, oxygen, or sulfur atoms; wherein aryl may be optionally substituted with 1 to 5 same or different $R_1$; or $Q_1$ and $Q_2$ are the same or different substituted C6-C10 aryl, wherein aryl may be optionally substituted with 1 to 5 same or different $R_4$; $R_4$ is independently selected from halogen, nitro, cyano, haloalkyl, C1-C4 alkyl or C1-C4 alkoxyl.

14. The method of claim 13 wherein $Q_1$ is hydrogen, $Q_2$ is straight or branched C1-C10 alkyl, or C3-C7 cycloalkyl; wherein the cycloalkyl may contain 1 to 2 carbon-carbon double bond or triple bond.

15. The method of claim 13 wherein $Q_1$ is hydrogen, $Q_2$ is phenyl or phenyl group optionally substituted with one to five same or different $R_2$; wherein $R_2$ is independently selected from hydroxyl, halogen, carboxyl, amino, nitro, cyano, trifluoromethyl, trifluoromethoxy, C1-C4 alkyl, C3-C7 cycloalkyl, C1-C4 alkoxyl, C1-C3 alkylene dioxy, C1-C4 alkoxylmethyl, amino substituted with mono- or di-C1-C4 alkyl, C1-C4 alkylsulphonyl, or benzoyloxy substituted with $R_1$.

16. The method of claim 13, where $Q_1$ is hydrogen, $Q_2$ is

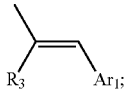

wherein $R_3$ is independently selected from hydrogen and C1-C4 alkyl;

$Ar_1$ is phenyl, or phenyl group optionally substituted with 1 to 5 same or different $R_2$; wherein $R_2$ is independently selected from hydroxyl, halogen, carboxyl, amino, nitro, cyano, trifluoromethyl, trifluoromethoxy, C1-C4 alkyl, C3-C7 cycloalkyl, C1-C4 alkoxyl, C1-C3 alkylene dioxy, C1-C4 alkoxylmethyl, amino substituted with mono- or di-C1-C4 alkyl, C1-C4 alkylsulphonyl or benzoyloxy substituted with $R_1$.

17. The method of claim 13, wherein $Q_1$ and $Q_2$ are phenyl, or different phenyl group optionally substituted with 1 to 5 same or different $R_4$; wherein $R_4$ is independently selected from halogen, C1-C4 alkyl, or C1-C4 alkoxyl.

18. The method of claim 13, wherein the compound is selected from the group consisting of:
2-methylene-5-(4-chlorobenzylidene)cyclopentanone,
2-methylene-5-(4-methoxybenzylidene)cyclopentanone,
2-methylene-5-benzylidene-cyclopentanone,
2-methylene-5-(4-methylbenzylidene)cyclopentanone,
2-methylene-5-(3-methoxybenzylidene)cyclopentanone,
2-methylene-5-(4-bromobenzylidene)cyclopentanone,
2-methylene-5-(2-methoxybenzylidene)cyclopentanone,
2-methylene-5-(4-ethoxybenzylidene)cyclopentanone,
2-methylene-5-(4-propoxybenzylidene)cyclopentanone,
2-methylene-5-(4-methanesulfonylbenzylidene)cyclopentanone,
2-methylene-5-(4-N,N-dimethylbenzylidene)cyclopentanone,
2-methylene-5-(2-hydroxy-4-methoxybenzylidene)cyclopentanone,
2-methylene-5-(3-hydroxy-4-methoxybenzylidene)cyclopentanone,
2-methylene-5-(3-methoxy-4-hydroxybenzylidene)cyclopentanone,
2-methylene-5-(2,3-dimethoxybenzylidene)cyclopentanone,
2-methylene-5-(2,4-dimethoxybenzylidene)cyclopentanone,
2-methylene-5-(3,4-dimethoxybenzylidene)cyclopentanone,
2-methylene-5-(3,4-methylenedioxy-benzylidene)cyclopentanone,
2-methylene-5-(3,5-dimethoxy-4-hydroxybenzylidene)cyclopentanone,
2-methylene-5-(3,5-di(t-butyl)-4-hydroxybenzylidene)cyclopentanone,
2-methylene-5-(3,4,5-trimethoxybenzylidene)cyclopentanone,
2-methylene-5-(3-methylbutylidene)cyclopentanone,
2-methylene-5-(4-hydroxybenzylidene)cyclopentanone,
2-methylene-5-(2-hydroxybenzylidene)cyclopentanone,
2-methylene-5-diphenylmethylenecyclopentanone,
2-methylene-5-[bis(4-methylphenyl)-methylene]cyclopentanone,
2-methylene-5-[bis(4-fluorophenyl)-methylene]cyclopentanone,
2-methylene-5-[(E)-3-phenylallylidene]cyclopentanone, and
2-methylene-5-(E)-2-methyl-3-phenylallylidene)cyclopentanone.

* * * * *

UNITED STATES PATENT AND TRADEMARK OFFICE
CERTIFICATE OF CORRECTION

PATENT NO. : 8,415,505 B2  
APPLICATION NO. : 12/867223  
DATED : April 9, 2013  
INVENTOR(S) : Linxiang Zhao et al.

Page 1 of 1

It is certified that error appears in the above-identified patent and that said Letters Patent is hereby corrected as shown below:

In the Claims

Column 30, Lines 19-22, Claim 6:
"2-methylene-5-[(E)-3-phenylallylidene]cyclopentanone, and 2-methylene-5-(E)-2-methyl-3-phenylallylidene)cyclopentanone." should read, --2-methylene-5-[($E$)-3-phenylallylidene)cyclopentanone, and 2-methylene-5-(($E$)-2-methyl-3-phenylallylidene)cyclopentanone.--.

Column 32. Lines 23-26, Claim 12:
"2-methylene-5-[(E)-3-phenylallylidene]cyclopentanone, and 2-methylene-5-(E)-2-methyl-3-phenylallylidene)cyclopentanone." should read, --2-methylene-5-[($E$)-3-phenylallylidene]cyclopentanone, and 2-methylene-5-(($E$)-2-methyl-3-phenylallylidene)cyclopentanone.--.

Column 34, Lines 46-49, Claim 18:
"2-methylene-5-[(E)-3-phenylallylidene]cyclopentanone, and 2-methylene-5-(E)-2-methyl-3-phenylallylidene)cyclopentanone." should read, --2-methylene-5-[($E$)-3-phenylallylidene]cyclopentanone, and 2-methylene-5-(($E$)-2-methyl-3-phenylallylidene)cyclopentanone.--.

Signed and Sealed this
Eighteenth Day of February, 2014

Michelle K. Lee
*Deputy Director of the United States Patent and Trademark Office*